US008073238B2

(12) United States Patent
Nakanishi et al.

(10) Patent No.: US 8,073,238 B2
(45) Date of Patent: Dec. 6, 2011

(54) MIXED INJECTION INSPECTION SYSTEM

(75) Inventors: Hirokazu Nakanishi, Kyoto (JP);
Hiroyuki Yuyama, Toyonaka (JP);
Satoshi Goto, Toyonaka (JP)

(73) Assignee: Yuyama Mfg. Co., Ltd., Osaka (JP)

( * ) Notice: Subject to any disclaimer, the term of this patent is extended or adjusted under 35 U.S.C. 154(b) by 635 days.

(21) Appl. No.: 12/281,612

(22) PCT Filed: Mar. 1, 2007

(86) PCT No.: PCT/JP2007/053922
§ 371 (c)(1),
(2), (4) Date: Sep. 3, 2008

(87) PCT Pub. No.: WO2007/100046
PCT Pub. Date: Sep. 7, 2007

(65) Prior Publication Data
US 2009/0161941 A1 Jun. 25, 2009

(30) Foreign Application Priority Data

Mar. 3, 2006 (JP) ................................. 2006-057367
Feb. 28, 2007 (JP) ................................. 2007-048634

(51) Int. Cl.
*G06K 9/00* (2006.01)
(52) U.S. Cl. ........................................ 382/141; 700/216
(58) Field of Classification Search ................... 385/141; 700/216, 236, 239, 244; 705/2–3
See application file for complete search history.

(56) References Cited

U.S. PATENT DOCUMENTS

2003/0179287 A1* 9/2003 Kozic et al. ................. 348/14.08
2008/0195416 A1* 8/2008 Tribble et al. ..................... 705/2

FOREIGN PATENT DOCUMENTS

| CN | 2311404 | 3/1999 |
|---|---|---|
| CN | 2598966 | 1/2004 |
| JP | 2000-092483 A | 3/2000 |
| JP | 2003-209821 A | 7/2003 |
| JP | 2004-70803 A | 3/2004 |
| JP | 2005-346552 A | 12/2005 |
| JP | 2006-050144 | 2/2006 |
| WO | WO 2004/112685 A1 | 12/2004 |

OTHER PUBLICATIONS

International Search Report for PCT/JP2007/053922, Mailed Mar. 27, 2007 (In English and Japanese. 2 pages).

* cited by examiner

*Primary Examiner* — Kara E Geisel
(74) *Attorney, Agent, or Firm* — Jones Day; Christopher C. Bolten

(57) ABSTRACT

Provided is a system for reducing burden on an inspector by making it possible to evaluate the operation of a mixed injection worker which is difficult to evaluate numerically at a place remote from the mixed injection work place. Provided is a mixed injection inspection system for inspecting a mixed injection work for mixing an injection drug by an inspector different from a mixed injection worker, the mixed injection inspection system including: a mixed injection work photographing device provided in a mixed injection work place and used to photograph the mixed injection work; an inspector side mixed injection work monitor provided in a place remote from the mixed injection work place and used to display the mixed injection work photographed by the mixed injection work photographing device; an inspector side input device provided in a place remote from the mixed injection work place and used to input instructions for the worker working at the mixed injection work place; and a mixed injection worker side display means for displaying to the mixed injection worker what has been input by the inspector side input device.

19 Claims, 20 Drawing Sheets

MIXED INJECTION INSPECTION MONITOR

| PATIENT ID | 00000001 | PATIENT NAME | YUYAMA TAICHIRO | | | | | | | DETAILS ON PATIENT |
|---|---|---|---|---|---|---|---|---|---|---|
| WARD | 4F EASTERN WARD | DEPARTMENT | UROLOGY DEPARTMENT | | | | | | | |

PATIENT INFORMATION

| | | ADJUSTMENT HOSPITALIZATION | | AGE | 33 | BODY SURFACE AREA | 53.0 | | |
|---|---|---|---|---|---|---|---|---|---|
| | | SLIP SECTION | | | | | | | |
| | | EXECUTION DATE | | GENDER | MALE | READ MODE (APPROVAL NUMBER) | | | |

PRESCRIPTION INFORMATION

| MEDICINE NOT COMPLETED | MEDICINE COMPLETED | ALL |
|---|---|---|

Rp 1-1 FIRST APPLICATION(COMPLETE)
IVH PIECE A-1
RANDA INJECTION 50mg 100ml       100mg
ONCE A DAY NOON
FROM 1 P.M.
ADJUSTMENT REQUEST
200ml/h
REPLACEMENT CYCLE: ONE HOUR

Rp 2-1 FIRST APPLICATION(COMPLETE)
IVH PIECE A-1
H-OSMISIN S INTRAVENOUS
INJECTION 2g                      1 BOTTLE
GLUCOSE INJECTION 5%
GLUNON 200 ml                     1 BOTTLE
ONCE A DAY EVENING
FROM 5. P.M.
200ml/h
REPLACEMENT CYCLE: ONE HOUR

G1

DETAILED INFORMATION

| DETAIL DISPLAY ORDER | NAME OF MEDICINE | PRESCRIPTION ORDER ▽ | DOSAGE | UNIT | pH VALUE | MIXTURE CHECK | MIXED INJECTION Grp | COMPLETE/ NUMBER | COMPULSORY INSPECTION | DISSOLUTION IMAGE | SKIP INSPECTION | SYRINGE INSPECTION |
|---|---|---|---|---|---|---|---|---|---|---|---|---|
| 1 | RANDA INJECTION 50mg 100m | | 100 | mg | 1.0 | | A | 1/2 | | | | |
| 2 | [TOTAL DOSE] | | 200 | ml | | | | | | | | |
| 3 | | | | | | | | | | | | |
| 4 | | | | | | | | | | | | |
| 5 | | | | | | | | | | | | |
| 6 | | | | | | | | | | | | |
| 7 | | | | | | | | | | | | |
| 8 | | | | | | | | | | | | |
| 9 | | | | | | | | | | | | |
| 10 | | | | | | | | | | | | |

G2 — B12

ADDITIONAL PRESCRIPTION INFORMATION

| SYRINGE DISSOLUTION IMAGE ACQUISITION | | | SYRINGE/WEIGHT INSPECTION MODE | | | RESERVATION MONITOR | GUIDE | ATTRIBUTE | ○ CONTINUOUS | ○ REPEATED | | |
|---|---|---|---|---|---|---|---|---|---|---|---|---|
| MOVING IMAGE MONITOR | | | | | | | | | ↑ | ↓ | INSPECTION MODE | COMMUNICATION INFORMATION |
| CANCEL MIXED INJECTION Grp | DIVIDE MIXED INJECTION Grp | LINE INSERTION | LINE DELETION | RE-EXECUTION | PRINTING AVAILABLE | REISSUE | | | | | RANDOM | NORMAL |
| F1 | F2 | F3 | F4 | F5 | F6 | F7 | F8 | F9 | F10 | F11 F12 | | |

MIXED INJECTION INSPECTION MONITOR

| PATIENT ID | 00000001 | PATIENT NAME | YUYAMA TAICHIRO |
|---|---|---|---|
| WARD | 4F EASTERN WARD | DEPARTMENT | UROLOGY DEPARTMENT |

PATIENT INFORMATION

| SLIP SECTION | ADJUSTMENT HOSPITALIZATION | AGE | 33 | BODY SURFACE AREA | 53.0 | DETAILS ON PATIENT |
|---|---|---|---|---|---|---|
| EXECUTION DATE | | GENDER | MALE | READ MODE (APPROVAL NUMBER) | | |

PRESCRIPTION INFORMATION

DETAILED INFORMATION

| DETAIL DISPLAY ORDER | PRESCRIPTION ORDER ▽ | | | | MIXTURE CHECK | | COMPULSORY INSPECTION | | CANCELED MEDICINE |
|---|---|---|---|---|---|---|---|---|---|
| | NAME OF MEDICINE | DOSAGE | UNIT | pH VALUE | MIXED INJECTION Grp | COMPLETE/NUMBER | DISSOLUTION IMAGE | | SYRINGE INSPECTION |
| 1 | RANDA INJECTION50mg 100ml | 100 | mg | 1.0 | A | 2/2 | ACQUIRE | | |
| 2 | [TOTAL DOSE] | 200 | ml | | | | | | |
| 3 | | | | | | | | | |
| 4 | | | | | | | | | |
| 5 | | | | | | | | | |
| 6 | | | | | | | | | |
| 7 | | | | | | | | | |
| 8 | | | | | | | | | |
| 9 | | | | | | | | | |
| 10 | | | | | | | | | |

MOVING IMAGE MONITOR

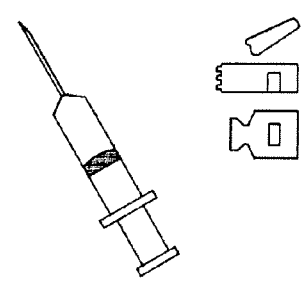

G3

ADDITIONAL PRESCRIPTION INFORMATION

| SYRINGE DISSOLUTION IMAGE ACQUISITION | | | | | | SYRINGE/WEIGHT INSPECTION MODE | | ○ CONTINUOUS | ○ REPEATED | | |
|---|---|---|---|---|---|---|---|---|---|---|---|
| CANCEL MIXED INJECTION Grp | DIVIDE MIXED INJECTION Grp | LINE INSERTION | LINE DELETION | RE-EXECUTION | PRINTING AVAILABLE | REISSUE | RESERVATION MONITOR | GUIDE | ATTRIBUTE | ← → | INSPECTION MODE RANDOM | COMMUNICATION INFORMATION NORMAL |
| F1 | F2 | F3 | F4 | F5 | F6 | F7 | F8 | F9 | F10 | F11  F12 | | |

MIXED INJECTION INSPECTION SYSTEM

TECHNICAL FIELD

The present invention relates to a mixed injection inspection system for inspecting a mixed injection work for preparing an injection drug by mixing medicines together and, in particular, to an inspection system allowing inspection of a mixed injection work at a place remote from the mixed injection worker, where inspection has not been conventionally performed.

BACKGROUND ART

The above-mentioned mixed injection work, which is directly related to the condition of the patient, has to be executed through very careful procedures. In particular, in the case of a powerful drug such as an anticancer agent, the agents constituting the materials thereof before mixing or the medicine prepared by mixed injection may, more often than not, harm the health of a person in normal health when taken inadvertently. In view of this, Japanese Society of Hospital Pharmacists, for example, has publicized "A Guideline for Preparing Injection drugs for Hospitalized Patients (December, 2000)," according to which, in order to secure the effectiveness and safety of a medicine, it is necessary to check the propriety of the prescription such as the applied dose, dosing method, dosing rate, and dosing system based on the patient information. When there is any doubt, it is necessary to refer to the prescribing physician before performing the medicine preparation work.

The injection drug is prepared by the following procedures and method. That is, the injection medicine order input by the doctor is output as an injection drug prescription within a predetermined period of time or at a predetermined time by a system totally controlled by a computer, and the medicine preparation is generally performed in the following order: 1. Prescription inspection and instruction regarding measurement (mixing); 2. Pre-inspection; 3. Measurement preparation; 4. Germ-free adjustment (mixing with infusion solution); 5. Post-mixing inspection and label attachment; 6. Counting (individual setting) and label affixation; and 7. Final inspection.

In this way, in the mixed injection work, inspection has to be performed for each of a number of stages taking safety into consideration. Above all, the above-mentioned steps of 2. Pre-inspection and 3. Germ-free adjustment are important. Regarding 3. Germ-free adjustment, checking (inspection) has to be performed at various stages of the method (checking of the medicines to be mixed, the way of mixing, the degree of oscillation, oscillation time, etc.). In particular, it is obvious that an error in the selection of the medicines used for mixed injection or an error in the amount of medicine leads to a fatal result. In view of this, in the pre-inspection, the medicine and the infusion solution prescribed and stored for the patient, and the medicine and the infusion solution to be actually subjected to mixed injection, are checked through comparison. Regarding the mixed injection work, there has conventionally been known a prescribed medicine preparation support system (Patent Document 1) in which there are provided a master database storing master data on a large number of medicines, and a preparation pattern storage means storing a plurality of types of medicine preparation patterns set beforehand, each preparation pattern indicating the procedures for preparing a plurality of kinds of medicine to be administrated to the patient at one time and accommodating the same in a support container and using as parameters a part or all of the following factors: presence/absence of solid medicine, presence/absence of liquid medicine, presence/absence of solvent, presence/absence of diluent, and the kind of supply container; the medicine preparation procedures, which includes a plurality of steps, include the step of measuring the initial weight of the supply container and the step of measuring the final weight of the supply container after preparation of the mixed injection, whereby the initial weight and the final weight are compared with each other to check whether the applied dose of the medicine constituting the mixed injection material has been proper or not.

In the conventional technology disclosed in Patent Document 1, the quantitative control of the medicines used are effected accurately as described above, and hence this technique is excellent as a prescription medicine preparation support system for an anticancer agent or the like, of which the quantitative control of medicines is effected with particular strictness.

Patent Document 1: JP 2004-208842 A

DISCLOSURE OF THE INVENTION

Problem to be Solved by the Invention

In mixed injection work, it is naturally important to attain a proper applied dose. However, as described above, it also involves an object of evaluation that is rather difficult to numerically evaluate, that is, the mixed injection work performed by the mixed injection worker, such as the way the medicines to be subjected to mixed injection are mixed, the degree of oscillation, and oscillation time, and the above-mentioned well-known conventional technology is of no use in the inspection of the mixed injection operation, which is difficult to evaluate numerically. Thus, in actuality of the prior art, in order to inspect the mixed injection work, which is difficult to express numerically, the inspector has to perform inspection by the side of the mixed injection worker from the beginning to the end of the mixed injection work.

It should be noted, however, that the inspector does not exclusively belong to a certain mixed injection worker but has to inspect the mixed injection work of a plurality of workers. Thus, in the above-mentioned method, in which the inspector has to perform inspection by the side of the worker, the inspector must go around from one worker to another for inspection. This means a considerable burden on the inspector.

In other words, this burden on the inspector will be cleared away when, for example, he can inspect different mixed injection operations one after the other while staying in a single inspection room.

Further, as described above, the operation of inspecting the mixed injection requires a very keen observation, and hence inspecting two operations at the same time may lead to an inspection error. Thus, when one inspector inspects a plurality of mixed injection works through a monitor, it is desirable to adopt a system in which the inspection of a plurality of works is not conducted simultaneously but in which the inspector always inspects a single mixed injection work through switching of the display on the monitor.

The present invention has been made in view of the above-mentioned problems in the prior art. It is an object of the present invention to provide a system which makes it possible to evaluate the operation of the mixed injection worker, which is difficult to evaluate numerically, at a place remote from the mixed injection work place, thereby mitigating the burden on the inspector. Another object of the present invention is to provide a system in which it is possible to execute visual inspection on a plurality of mixed injection works at a single place in a concentrated manner to thereby substantially improve the efficiency in inspection and, further, a system in which it is possible to inspect different mixed injection works one after another while staying in a place remote from the mixed injection work places. In a system as mentioned above, it is necessary to provide a mixed injection worker side monitor enabling the inspector to point out any error or the like in mixed injection work. When it is possible through this mixed injection worker side monitor to display mixed injection information including the medicine for mixed injection, the mixing procedures thereof, and instructions regarding the mixing processing, a single monitor can provide two different functions, which is advantageous from the economical point of view. Still another object of the present invention is to provide such an economical system.

Means for Solving the Problems

In order to achieve the above objects, there is provided, according to the present invention, a mixed injection inspection system in which a mixed injection work for mixing an injection drug is inspected by an inspector that is different from a mixed injection worker, the system connecting a mixed injection work place where the mixed injection worker stays and a place remote from the mixed injection work place, such as an inspection room where the inspector inspecting the mixed injection work stays, in which, at the place where the mixed injection worker stays, there is provided a mixed injection worker side display means for displaying for the mixed injection worker what has been input from an inspector side input device, and in which, in an inspection room or the like remote from the mixed injection work place, there are provided an inspector side mixed injection work monitor for displaying the mixed injection work photographed by a mixed injection work photographing device and an inspector side input device for inputting instructions for a worker working at the mixed injection work place. As a result, the inspector can inspect the mixed injection operation of the mixed injection worker photographed by the mixed injection work photographing device for photographing the mixed injection operation while staying in an inspection room or the like, which is remote from the mixed injection work place, by means of the inspector side mixed injection work monitor. In this respect, in the conventional inspection system, when performing the visual inspection of the mixed injection work, the inspector must remain all the time by the side of the mixed injection worker to inspect his work, and the inspector must always stays together with the mixed injection worker, and hence the inspector is obliged to walk around in all directions, whereas, in the present invention, the inspector can inspect the mixed injection work of the mixed injection worker while staying in an inspection room or the like, thus reliving the inspector of a large burden.

As described above, the conventional mixed injection inspection system involves an operation of a very low efficiency, whereas, according to the present invention, the inspector can monitor in a concentrated manner alone, in a different inspection room or the like, images of mixed injection work sent from a plurality of mixed injection work photographing devices placed at a plurality of mixed injection work places, and hence it is possible for a single inspector to inspect the operations of a plurality of mixed injection workers, thus succeeding in markedly enhancing the inspection efficiency. As described above, the operation of inspecting mixed injection work requires a very keen observation, and hence the inspection of two operations at the same time may lead to an inspection error. Thus, in another embodiment of the present invention, there is provided a system in which, even when a single inspector inspects a plurality of mixed injection works through a monitor, the inspection of different mixed injection works is not conducted at the same time but is always concentrated on a single mixed injection work through switching the display on the monitor. While in actuality single inspector monitors single mixed injection work at a given point in time, when the inspection of one mixed injection work is completed, the inspector can continue to monitor another mixed injection work while staying in an inspection room or the like upon request from the next mixed injection worker without having to move to a different mixed injection work place. In this sense, in the present invention, there is established a relationship of one to many.

Further, an actual mixed injection inspection requires mutual understanding between the mixed injection worker and the inspector. For example, when it is judged that the medicine mixing movement is rather slow, the inspector must instruct the worker to shake the container harder, and when it is determined that the operation satisfies the inspection provisions, the inspector must send a message to the mixed injection worker that he may end the mixed injection work because the work is regarded as acceptable. Otherwise, the inspection itself would be no use. Thus, as described above, in this invention, there is provided at the mixed injection work place a mixed injection worker side display means for displaying for the mixed inspection worker what has been input by the inspector side input device, at the same time, there are provided in an inspection room or the like remote from the mixed injection work place an inspector side mixed injection monitor for displaying a mixed injection work photographed by the mixed injection photographing device, and an inspector side input device for inputting instructions for the mixed injection worker working at the mixed injection work place, thus enabling mutual understanding between the mixed injection worker and the inspector.

In another embodiment of the present invention, there are provided a medicine management server storing mixed injection information including the medicine for the mixed injection, the mixing procedures thereof, and instructions regarding the mixing processing, and a mixed injection worker side mixed injection information monitor provided at the mixed injection work place connected to the medicine management server and adapted to display the mixed injection information. In the prior art, it is necessary to take a sheet of paper such as an injection slip with mixed injection information into the mixed injection work place, and the sheet of paper such as the injection slip suffers fading of printed information due to spraying of a disinfectant such as alcohol, or is moistened to be wrinkled, making the letters hard to read. However, in the present invention, such a problem is cleared away due to the above-mentioned mixed injection worker side mixed injection information monitor.

According to still another embodiment of the present invention, there is provided a mixed injection inspection system in which the mixed injection worker side mixed injection information monitor also serves as the mixed injection worker side display means. Of course, with such a monitor, it is possible to very easily execute the processing of successively erasing procedures that have been completed, and hence the burden on the mixed injection worker is reduced and, at the same time, the operation is optimized. As described above, according to the present invention, it is basically necessary to provide a mixed injection worker side display means to enable the inspector to point out any error in mixed injection work. When this mixed injection worker side display means can display mixed injection information including the medicine for mixed injection, the mixing procedures thereof, and instructions regarding the mixing processing, that is, when the mixed injection worker side display means also serves as the mixed injection worker side mixed injection information monitor, it is possible for a single monitor (display means) to provide the above-mentioned two functions, thus making it possible to realize an economical system.

According to still another embodiment, there is provided a construction in which the inspector side mixed injection work monitor can display through switching images from a plurality of mixed injection work photographing devices. In this way, images from the plurality of mixed injection work photographing devices are displayed through switching, whereby it is possible to prevent occurrence of careless mistakes due to performing a plurality of inspections at one time. Alternatively, it is also possible to adopt a construction in which the inspector side mixed injection work monitor can effect switching display of images from the above-mentioned mixed injection work photographing devices upon request from the mixed injection worker side. With this construction, when the mixed injection worker wishes to illustrate the inspector different images one after another, inspection is possible with the images being switched efficiently, and hence inspection can be conducted smoothly on a wide range of operations and the inspection efficiency is enhanced.

Effects of the Invention

According to the present invention, the operation of a mixed injection worker, which is an evaluation factor difficult to evaluate numerically and which, otherwise, has to be inspected by the side of the mixed injection worker, can be visually inspected while staying in an inspection room or the like remote from the mixed injection worker, and hence the burden on the inspector is markedly mitigated, and, at the same time, such visual inspection can be performed at a single position in a concentrated manner on a plurality of mixed injection works, and hence it is possible to markedly enhance the inspection efficiency.

BEST MODE FOR CARRYING OUT THE INVENTION

In the following, for the present invention to be understood, an embodiment of the present invention is described with reference to the accompanying drawings. The following embodiment is only given by way of example, and does not restrict the technical scope of the present invention. Here, FIG. 1 is a schematic flowchart to which the system of the present invention is applicable, illustrating the procedures of request for injection drug prescription to injection drug administration. FIG. 2 is a schematic diagram illustrating hardware for supporting the system of the present invention. FIG. 3 is a schematic flowchart illustrating mixed injection work. FIG. 4 is a flowchart illustrating information processing procedures of a medicine management server supporting mixed injection work and a mixed injection worker side display means in relation to a control means. FIG. 5 is a diagram illustrating an initial menu in a mixed injection worker side display means or inspector side mixed injection work monitor. FIG. 6 is a diagram illustrating an example of an initial screen when a mixed injection inspection monitor menu or a remote inspection monitor menu is selected in the mixed injection worker side display means or the inspector side mixed injection work monitor. FIG. 7 is a diagram illustrating how patient information is displayed in the mixed injection worker side display means or the inspector side mixed injection work monitor. FIG. 8 is a diagram illustrating a screen displaying a syringe constituting an inspection object. FIG. 9 is a diagram illustrating a screen displaying detailed mixed injection information in the state of FIG. 8. FIG. 10 is a diagram illustrating the display screen of a remote inspection monitor. FIG. 11 is a front view of an example of a safety cabinet for use in mixed injection work. FIG. 12 is a perspective view of the safety cabinet illustrated in FIG. 11. FIG. 13 is a perspective view illustrating in detail the door portion of the safety cabinet. FIG. 14 is a perspective view illustrating how work is conducted in the safety cabinet. FIG. 15 is a perspective view illustrating how work is conducted in another safety cabinet. FIG. 16 is a perspective view illustrating how work is conducted in still another safety cabinet. FIG. 17 is a general perspective view of a pre-inspection apparatus. FIG. 18 is a front view of the pre-inspection apparatus. FIG. 19 is a rear view of the pre-inspection apparatus. FIG. 20 is a plan view of the pre-inspection apparatus.

First, referring to the flowchart of FIG. 1, the outline of the procedure flow from prescription order to medicine administration is described, which is a background technique to which the system of the present invention that has undergone pre-inspection as described above is applied. The processing is started with the processing on the pharmacist side. The procedures are numbered as T1, T2, . . . . When the prescription/adjustment-slip of the injection drug prepared on the doctor side is received (i.e., when the order is received (T1)), the pharmacist performs inspection for any error in the received injection prescription (T2). This process is the pre-inspection described above.

Subsequently, the prescription slip of the injection drug according to the above prescription is prepared (T3). When the prescribed injection drug is not an object of mixed injection (T4), preparation is directly conducted without mixed injection processing, and the medicine is delivered (T6) after inspection (T5). When the injection drug described in the prescription is an object of mixed injection (T7), the medicines for mixed injection are prepared, and inspection is conducted (T9) on the names and number of the prepared medicines along with a medicine total sheet (T8). In the mixed injection work described below, it is necessary to check whether the medicines are the right ones, and for that purpose, there is prepared a label with the name of the patient and details on the medicines (T10). The inspected medicines and the label are stored in a set (T11).

The preparation for the mixed injection work is conducted as described above. Usually it is completed on the day before the mixed injection work. Here, what is mentioned on the label including the mixed injection data, such as the inspection state, the medicines prepared, the ID of the patient, the name of the patient, and the day on which mixed injection is to be conducted, is all input at the pharmacist side terminal, sent to a medicine management server 1 described below, and stored in a mixed injection information database 3. Next, the actual mixed injection work is conducted immediately before the administration in order to prevent loss of the effect of the medicines due to progress in chemical reaction of the medicines. In performing mixed injection work, a combination of the prepared medicines and the label set on the previous day based on identification information such as the name of the patient is paid out. The prepared medicines and the label in a set are inspected (pre-inspected) for their propriety for mixed injection (T12). For example, in the detailed information in FIG. 7, the figures of ½ in the "completion/number" section indicates that the inspection of one of two medicines has been completed, that is, the condition of the pre-inspection. After that, mixed injection work is executed by the mixed injection worker (T13). At this time, in order to check whether the mixed injection work is being properly conducted, not only the amount of medicine used but also the mixed injection operation is inspected. The present invention relates to an inspection system for this actual mixed injection operation, which is described in detail below. During the mixed injection work, sampling inspection is executed as needed also on the dissolution solution undergoing mixed injection (T14). For example, when dissolution is needed for mixed injection, at the point in time when the dissolution solution is sampled, the mixed injection worker depresses a syringe dissolution image acquisition button B14 (see FIGS. 8 and 9), there is obtained a still image of the syringe at the point in time when the dissolution solution has been taken out. Further, as illustrated in FIG. 8, the word "acquisition" is displayed in the dissolution image section displayed in the detailed information column in FIG. 8. When the mixed injection work is completed, the requisite inspection is conducted on the prepared injection drug obtained through mixed injection (post-inspection) (T15). In this post-inspection, which is the final inspection, an inspection requirement is issued from the mixed injection worker. More specifically, this is executed when the mixed injection worker re-depresses the inspection start button B12 in the detailed information in FIG. 9. When the above-mentioned inspection requirement is transmitted, on the remote inspection monitor side illustrated in FIG. 10, the inspector depresses the button of the apparatus (indicated on the upper side in FIG. 10) on which inspection is to be performed by the inspector. When this signal is received, a preparation room control portion 19 displays the word "inspection" under the syringe inspection in the detailed information in the screen of a mixed injection worker side display means 23 illustrated in FIG. 9 (see FIG. 2). This display is changed to "OK" by further depressing an approval button B15 in the remote inspection monitor on the inspector side illustrated in FIG. 10. At this time, the dissolution image cell in the detailed information in the mixed injection inspection monitor screen in FIG. 10 is also changed from "acquisition" to "OK". The medicine thus undergone the final inspection is delivered (T16) and administrated (T17).

Here, the pre-inspection apparatus used in the pre-inspection is described. The pre-inspection is a processing for confirming (checking), before the mixed injection work, whether the liquid medicines or the like to be mixed together are the same as those to be administrated thereafter to the patient, that is, whether the medicines and the infusion solution to be subjected to mixed injection are the same as the medicines and the infusion solution as set forth on the registered prescription for the patient. This pre-inspection is very important since, when there is an error in this checking, the mixed injection work is basically impossible. In the mixed injection work, a plurality of medicines (e.g., powder and liquid medicine) are mixed together, or a liquid medicine is mixed with an infusion solution such as a physiological salt solution or glucose. The liquid medicine is usually contained in an ampoule or a bottle, and the infusion solution such as a physiological salt solution is usually contained in a plastic infusion solution bag. In either case, inspection is performed as to whether the liquid medicine and the infusion solution are the right liquid medicine and the right physiological salt solution by reading the labels, barcodes, or the like affixed to the surfaces of the containers. FIG. 17 is a general perspective view of the pre-inspection apparatus 50. Roughly speaking, the pre-inspection apparatus 50 includes a medicine inspection portion 51 on the apparatus front side for inspecting the medicines in ampoules, medicine bottles, or the like, an infusion bag inspection portion 53 for inspecting an infusion bag containing the physiological salt solution or the like, and a lower drive portion 55 accommodating a component for driving the medicine inspection portion 51.

As illustrated in FIG. 18, the medicine inspection portion 51 has, inside a cover 83 that can be opened and closed, two rotary rollers 59a, 59b on which an ampoule 57 is placed horizontally for rotation. As illustrated in FIG. 20, the rotary rollers 59a, 59b are arranged horizontally side by side so that they can rotate with the ampoule 57 placed thereon. A speed reduction motor 61 for low speed rotation is connected to one rotary roller 59a. Further, a belt 63 is stretched between the rotary roller 59a and the other rotary roller 59b, the rotary roller 59b being driven to be rotated in the same direction and at the same RPM as the rotary roller 59a by the torque transmitted by the belt 63.

Between the rotary rollers 59a and 59b, there exists some space 65 (see FIG. 20). As can be seen from FIG. 20, below the space 65, a reflection mirror 67 (see FIG. 18) at an angle of 45 degrees is fixed in position so as to optically reflect via the space 65 the images of the barcode or label affixed to the ampoule 57 rotated by the rollers 59a, 59b. Further, the image of the barcode or the like on the surface of the ampoule 57 reflected by the reflection mirror 67 is reflected by the reflection mirror 67, and effects image formation on a line camera 69 provided in the optical axis thereof before being photographed by the line camera 69. In this way, through rotation of the rotary rollers 59a, 59b by the speed reduction motor 61, the ampoule 57 is rotated by the rotary rollers 59a, 59b, and the entire image of the barcode, label, or the like on the surface of the ampoule is read by the line camera 69. The read image is transmitted to a control computer (not shown), and the letters are recognized by a well-known method such as image recognition, whereby a judgment is made as to whether the object of inspection is the right medicine or not based on data such as the name of the patient, treatment, and the name of medicine.

As illustrated in FIG. 20, a belt 73 is wrapped around two vertically provided pulleys 71a, 71b, and a bracket 75 is fixed to the belt 73. An ampoule push-out member 79 (see FIG. 18) is provided on the bracket 75 through the intermediation of a horizontal mounting bar 77. When the pulleys 71a, 71b are rotated by a motor M, the belt 73 runs, and the ampoule 57 is pushed by the ampoule push-out member 79 mounted to the belt 73 through the intermediation of the mounting bar 77 before being discharged into a box 81 and conveyed to a mixed injection work room, where mixed injection work described below is conducted.

Further, as described below, also regarding an infusion solution bag 85 illustrated in FIG. 18, it is possible to conduct inspection by reading a prescription, a label or barcode 88 on the surface thereof by the infusion bag inspection portion 53. The infusion bag inspection portion 53 is provided with a bag placing tray 87 including a transparent plate and swingable around a horizontal support bar 86. As illustrated in FIG. 19, a weight 89 is attached to an end portion 87a of the bag placing tray 87. Further, due to the weight 89, when no infusion solution bag 85 is placed, the bag placing tray 87 maintains an inclined state in which an end portion 87b on the opposite side is somewhat raised. A detection member 91 is attached to the lower surface of the end portion 87b. Further, a frame below the detection member 91 is provided with a photo sensor 93 which is shielded from light through descent of the detection member 91 and which can sense the descent of the detection member 91. Further, as is apparent from FIG. 17, there is provided a barcode reader 97 which is adjacent to the bag placing tray 87 and which rotates around a horizontal pin 95 in the direction of the arrow Y to read the barcode affixed to the infusion solution bag 85 placed on the bag placing tray 87.

Thus, before or after or simultaneously with the reading of the ampoule 57, the operator places the infusion solution bag 85 on the bag placing tray 87. Then, the bag placing tray 87 is inclined (lowered) due to the weight of the infusion solution bag 85, and the detection member 91 is detected by the photo sensor 93, whereby a computer (not shown) connected to the photo sensor 93 detects the placing of the infusion solution bag 85 through a signal from the photo sensor 93. On the other hand, the barcode reader 97 is swung automatically or manually around the horizontal pin 95, whereby the reading portion thereof is swung to a position where the barcode of the infusion solution bag 85 can be read. Then, the barcode is read, and the data is stored in a computer for letter recognition. The computer checks the data in light of data, such as the name of the patient, the treatment, and the name of the infusion solution, making it possible to correctly judge whether the right infusion solution is being supplied or not. Regarding the image of the label affixed to the surface of the infusion solution bag 85, the reading is effected as follows: as is apparent from FIG. 19, the infusion solution bag 85 is placed on the transparent bag placing tray 87 with its surface facing downwards, whereby the image is read by the label camera 90 via the reflection mirror 88 inclined by 45 degrees below the bag placing tray 87, and is decoded as letter information by the computer connected to the label camera 90 before being checked (inspected) in light of information registered beforehand. While in the above-mentioned embodiment solely label reading is effected on the ampoule 57, it goes without saying that it is also possible to affix a barcode to the ampoule, causing it to be read by a barcode reader. Further, the above method of reading the label, the prescription, or the barcode is only given by way of example. It is also possible, for example, to adopt a method in which checking is made by reading various items of information such as the name of the liquid medicine and the name of the patient stored in an IC chip through communication with an IC chip such as an RFID chip attached to the ampoule, infusion solution bag or the like. such a method is also covered by this embodiment.

As is apparent from what has been described above, by using the above-mentioned pre-inspection apparatus 50, the operator can check (inspect) automatically or semi-automatically whether the medicine or the infusion solution paid out is the medicine or the infusion solution to be subjected to mixed injection or not, and hence it is possible to completely prevent selection of the wrong medicine or infusion solution.

Next, a mixed injection inspection system according to the embodiment of the present invention is described. Prior to a detailed description, an outline of the system is described. Basically, in this mixed injection inspection system, the mixed injection work for mixing injection drugs is inspected by an inspector different from the mixed injection worker. In particular, it is a system that is novel in that the mixed injection operation can be inspected even when the mixed injection worker and the inspector do not stay together all the time. For this purpose, in the embodiment of the present invention, a mixed injection operation photographing device (e.g., a CCD camera described below) for photographing the mixed injection work is provided in the mixed injection work place to photograph the mixed injection operation. The image of the mixed injection operation taken by this mixed injection work photographing device is transmitted to an inspection room remote from the mixed injection work place. In the inspection room, there is provided an inspector side mixed injection work monitor for displaying the mixed injection work as photographed by the mixed injection work photographing device, and the mixed injection work is displayed to the inspector.

Further, in the inspection room, there is provided an inspector side input device for inputting instructions for the worker working at the mixed injection work place. On the other hand, in the mixed injection work place, there is provided a mixed injection worker side display means for displaying to the mixed injection worker what has been input by the inspector side input device. According to the inspection result input from the inspector side input device (result of the judgment as to whether the mixed injection work is being correctly conducted or not), the mixed injection work is corrected, or allowed to continue. As a result, even when the inspector is not at the mixed injection work place, the inspector can conduct inspection including inspection to check the mixed injection operation for its propriety.

Further, there is provided a medicine management server storing mixed injection information including the medicine for mixed injection, the mixing procedures thereof, and instructions regarding the mixing process. Further, in the mixed injection work place, there is provided a mixed injection worker side mixed injection information monitor connected to the medicine management server and serving to display the mixed injection information, whereby the mixed injection worker can perform mixed injection work while watching the mixed injection worker side mixed injection information monitor, and hence there is involved no such problem as the injection slip or the like getting wet with a disinfectant or the like to become hard to read.

The mixed injection worker side mixed injection information monitor may also serve as the mixed injection worker side display means. This makes it possible to omit the monitor, which is economical. It is also possible for the inspector side mixed injection work monitor to display images from a plurality of the mixed injection work photographing devices. Since it is possible to inspect the mixed injection work of a plurality of persons with a single inspector side mixed injection work monitor, the burden on the inspector is markedly relieved.

In this case, when the inspector side mixed injection work monitor can display images from a plurality of the mixed injection work photographing devices one by one through switching, it is possible to avoid the risk of causing an inspection error by performing a plurality of inspections at one time.

[General System Construction] The outline of the mixed injection inspection system is as follows. First, the hardware construction of the mixed injection inspection system is described with reference to from FIG. 2 onward. As illustrated in FIG. 2, this system includes as the central component the medicine management server 1 connected to the mixed injection information database 3 storing mixed injection information including the medicine for mixed injection, the mixing procedures thereof, and instructions regarding the mixing process. An examination and treatment database 5 operated by the doctor is connected to the medicine management server 1. Further, an inspection room side control section 9 is connected to the medicine management server 1. An inspector side mixed injection work monitor 11 for displaying images photographed by a mixed injection work photographing device 21 described below, and an inspector side input device 13 for inputting instructions for the worker working at the mixed injection work place are connected to the inspection room side control section 9. The inspection room side control section 9, the inspector side mixed injection work monitor 11, and the inspector side input device 13 are provides in a place remote from the mixed injection work place described below, for example, within the inspection room 15.

Inside a clean room 18, which is different from the inspection room 15, there are provided one or a plurality of safety cabinets and clean benches 17a, 17b, 17c, . . . . Further, in the safety cabinets and clean benches 17a, 17b, 17c, . . . (hereinafter referred to as adjustment rooms 17), there are provided adjustment room control sections 19 connected to the medicine management server 1, respectively. A mixed injection work photographing device 21 such as a CCD camera for photographing the mixed injection work, and a mixed injection worker side display means 23 such as a monitor for displaying to the mixed injection worker what has been input by the inspector side input device 13 are connected to each adjustment room control section 19. Each mixed injection worker side display means 23 is connected to the medicine management server 1 via the adjustment room control section 19, and can display instructions from the inspector such as inspection approval or inspection NG input from the inspector side input device 13. Further, each mixed injection worker side display means 23 is connected via the adjustment room control section 19 to the medicine management server 1 connected to the mixed injection information database 3, and can display various items of mixed injection information. That is, the mixed injection worker side display means 23 also serves as a mixed injection worker side mixed injection information monitor for displaying the mixed injection information. This helps to achieve a reduction in monitor cost. Of course, it is also possible to provide each monitor separately. In the embodiment described below, the display means also serves as the monitor.

The medicine management server 1 is connected to all of the plurality of adjustment room control sections 19.

Thus, the inspector side mixed injection work monitor 11 can display through switching photographed images from the plurality of mixed injection work photographing devices 21 connected to the adjustment room control sections 19 via the inspection room side control section 9, the medicine management server 1, and the adjustment room control sections 19. The method of switching is described below. The mixed injection worker side display means 23 provided in the adjustment rooms 17 are connected to the inspector side input device 13 via the adjustment room control sections 19 and the medicine management server 1, and can display, for example, a judgment of the inspector, input from the inspector side input device 13.

[Construction of the Adjustment Rooms] Next, the specific construction of the adjustment rooms 17 is described with reference to FIGS. 11 through 16. While in this example the adjustment rooms 17 are safety cabinets, the adjustment rooms 17 may also be clean benches or the like. As illustrated in FIGS. 11 and 12, each adjustment room 17 as a safety cabinet has, at a position substantially in the middle in the vertical direction, a work room 33 whose front side is partitioned by a glass door 31. Due to the glass door 31, the work room 33 and the worker are separated from each other, thus preventing the worker coming into direct contact with the medicine.

An opening portion 35 is formed at the lower end of the glass door 31 is, through which the worker puts his hand into the work room 33 to perform mixed injection work. A momentary dimming glass 31a is attached to the glass door 31, which is an example of the mixed injection worker side display means 23. The momentary dimming glass 31a includes a transparent liquid crystal or the like, which is a well-known monitor device such as a transparent liquid crystal type display device or a reflection type liquid crystal display device which can display characters and other images on a glass by energizing a transparent matrix-like electrode to cause a change in the polarization state of the energized portion. Further, the momentary dimming glass 31a may be provided with some auxiliary light source. As described above, the details of the momentary dimming glass 31a are well-known, and hence a description thereof is omitted. Since the momentary dimming glass 31a is a transparent object, the worker can conduct mixed injection work while observing the object of work within the work room 33 through the momentary dimming glass 31a, reading the images such as characters drawn on the momentary dimming glass 31a. FIG. 13 illustrates how an image K is displayed on the momentary dimming glass 31a.

Further, as illustrated in FIG. 14, within the work room 33, there is provided a CCD camera 21a, which is an example of the mixed injection work photographing device 21. As illustrated in FIG. 14, the worker can hold up the object of work (which, in this case, is a syringe S sucking the medicine) before the CCD camera 21a to enable photographing by the CCD camera 21a. While the mixed injection worker side display means 23 may be the momentary dimming glass 31a as described above, it may also be a liquid crystal display 23b attached to the inner depth wall 37 of the work room 33 as illustrated in FIG. 15. Alternatively, it is also possible to adopt a display means such as a micro display including a transparent liquid crystal type display device or a reflection type liquid crystal display device incorporated into spectacles or a head set for the worker. Such a display including an electronic apparatus is very convenient in that it does not contaminate the environment. Further, in particular when using a medicine free from environmental contamination, it is also possible to adopt, instead of the above-mentioned display, a paper instruction slip 33c as illustrated in FIG. 16. Reference numeral 39 in FIG. 11 is an HEPA filter for cleaning the air inside the work room 33 before discharging the same.

[Mixed Injection Procedures] Next, details of the mixed injection work, indicated at T13, are described with reference to from FIG. 3 onward. Numerals S1, S2, . . . indicate the processing procedures. FIG. 3 is a flowchart illustrating all the works including procedures before and after mixed injection. FIG. 4 illustrates the procedures of mixed injection. Prior to the work, the mixed injection worker inputs the patient ID and mixed injection date to a terminal connected to the medicine management server, and obtains the medicine for mixed injection and the solvent thereof from the pharmacist (S1) before entering the clean room 18 with them. After that, the worker sits before a designated predetermined safety cabinet or clean bench (adjustment room 17), and puts the medicines he has brought in the work room 33.

In the state in which no work is being conducted, the inspector side mixed injection work monitor 11 and the mixed injection worker side display means 23 display the initial menu window of the mixed injection inspection system as illustrated in FIG. 5. While it is basically possible for the inspector side mixed injection work monitor 11 and the mixed injection worker side display means 23 to display the same window, they may also display different windows. While in this embodiment substantially the same window is displayed, there are partial differences in the window (e.g., FIG. 10). When the mixed injection worker depresses a mixed injection inspection monitor button B1 of FIG. 5, the mixed injection inspection monitor window as illustrated in FIG. 6 is displayed on the mixed injection worker side display means 23. At this stage, no setting has been made yet, and hence all the boxes are blank yet. To conduct mixed injection, the worker inputs information determining the details of the mixed injection, and depresses enter key. The details of the mixed injection are determined by inputting, for example, the patient ID and the execution date. As described with reference to the prescription order procedures of FIG. 1, at this time, the mixed injection information such as the patient ID, the name of the patient, the mixed injection execution date, and the administration execution date are listed on the label, and stored in the mixed injection information database 3 connected to the mixed injection management server 1, and hence, as stated above, when the worker inputs data such as the patient ID and the mixed injection execution date at an input portion (not shown) provided in the mixed injection worker side display means 23, all the mixed injection information related to this mixed injection is searched, and, as illustrated in FIG. 7, the patient information is displayed in the patient information box in the mixed injection information monitor window (S2).

When all the buttons (B11) in the prescription information box on the left-hand side of the window of FIG. 6 are depressed, all the information on the medicines to be subjected to mixed injection prescribed for this patient and stored in the mixed injection database 3 is displayed in the prescription information box G1 as illustrated in FIG. 7. Further, of the medicines displayed in the prescription information box G1 as described above, the medicine for which preparations for mixed injection have been completed (e.g., in this case, 100 mg of a solution of 50 mg of Rp1-1 randa injection) is displayed in the detail display box G2 on the right-hand side. All of these items of information are obtained by searching the mixed injection information database 3. When the details on the mixed injection to be conducted have been thus displayed on the mixed injection worker side display means 23, the mixed injection worker checks the mixed injection drug placed in the work room 33 and the label affixed thereto along with what is displayed on the mixed injection worker side display means 23, thereby executing pre-inspection prior to the mixed injection work (S3). This work is conducted manually.

While the mixed injection detailed information box of FIG. 7 only displays one Rp, that is, the prescription of one injection drug, when mixed injection of a plurality of injection drugs is required, a plurality of prescriptions are displayed. Next, mixed injection operation is started (S4). The mixed injection work and the operation of inspecting the same are conducted according to the procedures of FIG. 4. These procedures are mainly conducted in the adjustment room control section 19 on the mixed injection worker side and the inspection room side control section 9. The process is started with a procedure for checking the inspector in S11. Here, the inspector in the inspection room 15 called by an appropriate method is checked. Usually, the inspector depresses the remote control inspection monitor button B2 of the initial menu illustrated in FIG. 5 at the inspector side input device 13 connected to the inspection room side control section 9 in the inspection room to thereby input his ID, password or the like, whereby it is made sure that he is the proper inspector. Thus, in the checking procedure of S11, the ID, password or the like that has already been input as described above is checked along with the ID, password or the like of the previously designated inspector through reading of a barcode or the like on the label, whereby a judgment is made as to whether this inspector is the one to perform the inspection. Naturally, some other method is also acceptable.

When it is made sure that he is the proper inspector, the inspection start button B12 in the mixed injection inspection monitor window illustrated in FIG. 7 is waited for to be depressed (S12). The depression of the inspection start button B12 means the so-called request for inspection. When the moving image monitor button B13 is depressed (turned on in S12), the driving of the CCD camera 21a, which is an example of the mixed injection work photographing device provided in the work room 33, is started. At the same time, an image of the syringe, the medicine bottle, the medicine tube or the like photographed by the CCD camera 21a is displayed in the moving image monitor window G3 displayed at the left-hand end of FIG. 8.

Further, the adjustment room control section 19 (inspection room side control section 9) searches the mixed injection information database 3 based on the patient ID or the like via the medicine management server 1, and details on mixed injection as illustrated in FIG. 9 are displayed in the detailed information box G4 (S14). The details on mixed injection include, for example, the details of medicine and the solvent that are the object of mixed injection and instructions such as mixed injection procedures, and the mixed injection worker performs mixed injection work while referring to the details. In this case, there is no need to read a mixed injection prescription or instructions written on a paper sheet, and hence there are involved no such problems as the disposal of contaminated paper sheet and the letters being hard to read due to soiling of the paper sheet. Further, it is also possible to input any items noticed by the worker on the spot, and hence the effect of reducing errors in post-treatment is to be expected.

Next, the adjustment room control section 19 waits for the mixed injection start instruction to be input (S15). For example, it is possible to adopt a system in which, when the request for inspection is issued from the mixed injection worker as described above (i.e., through depression of the inspection start button B12), a beep sound is generated in the inspection room side mixed injection work monitor 11 connected to the inspection room side control section 9, and in which the beep sound is not canceled unless the inspector depresses some machine number (displayed in the upper section of FIG. 10 and set for each adjustment room 17) button. That is, the depression of the machine number button constitutes the mixed injection start instruction. When this mixed injection start instruction is issued, the mixed injection worker starts mixed injection work (S16). The mixed injection is conducted in accordance with the mixed injection procedures and instructions displayed on the window. In particular, in this case, the process resides in mixing an injection in a syringe with a solvent, and hence the object of inspection is how the medicine is dissolved in the syringe and how the syringe is shaken by the worker. At this time, in order to obtain an in-syringe dissolution image, the inspector depresses the in-syringe dissolution image acquisition button B14. When a signal indicating the depression of this button is received (ON in S17), the adjustment room control section 19 sends an image of the syringe S obtained by the CCD camera 21a to the inspection room side control section 9. The inspection room side control section 9 displays this image on the inspector side mixed injection work monitor 11. More specifically, this image is displayed in the moving image monitor box G6 of FIG. 10.

During this mixed injection work, it is possible for the inspector to transmit instructions regarding the mixed injection work to the worker as needed through a microphone, a beep sound, or the like. For example, the inspector gives an instruction necessary for inspection, telling the worker to shake the syringe harder, to bring the syringe closer to the camera, etc. Of course, when there is performed an operation not in accordance with the mixed injection procedures and instructions displayed in the detailed information box G4, an instruction to re-perform the procedures is transmitted. When it is determined that the mixed injection process has reached the final stage, the inspector or the worker depresses the inspection start button B12 of FIG. 9 (ON in S19). To make the most of the use of a camera, the inspector may instruct the mixed injection worker to place the empty bottle used within the photography range so that the inspector can visually recognize the medicine that has been mixed or dissolved. In this case, the empty bottle B0 or the like is displayed in the moving image monitor box G5 as illustrated in FIG. 10, making it possible to execute the inspection accurately as if the inspector is performing inspection by the side of the mixed injection worker.

Apart from the above-mentioned inspection of the mixed injection operation, it is naturally also necessary to inspect the solvent in terms of quantity or quality. For this purpose, when the inspection start button B12 is depressed (ON in S19), a dissolution amount inspection acquisition image indicating the condition of the solvent in the syringe is displayed on the left-hand side dissolution amount inspection acquisition window G6 in the lower right-hand side portion of FIG. 10. At the design stage of the system or prior to this mixed injection work, images of the solvent corresponding to various degrees of dissolution are stored in the dissolution amount master of the mixed injection information database 3 connected to the medicine management server 1. When a signal indicating the depression of the inspection start button B12 is received, the inspection room side control section 9 selects the solvent image corresponding to the present degree of dissolution from the dissolution amount master and displays the solvent image in the right-hand dissolution amount master information box G7 in the lower right-hand section of FIG. 10 (S20). The inspector can compare with each other the dissolution amount inspection acquisition image and the image of the dissolution amount master to execute inspection regarding the solvent amount.

When it is determined that the inspection has been thus completed, the inspector depresses either the approval button B15 of FIG. 10 or the NG button B16 indicating disapproval. When a signal indicating the depression of one of these buttons is received, the inspection room side control section 9 makes a judgment as to whether the approval button B15 has been depressed (ON in S21) or the NB button B16 has been depressed (ON in S22). As long as none of these buttons has been depressed, one of them is waited for being depressed. When the approval button B15 is depressed, the syringe image displayed on the inspector side mixed injection work monitor 11 at that time is saved as a still image. Further, when the mixed injection history inquiry menu of FIG. 5 is executed, it is possible to refer to the image thus saved. As a result, it is possible to check the mixed injection history of an arbitrary medicine. Of course, it is also possible to save a moving image illustrating mixed injection operation, thus making it possible to refer to the image as the mixed injection history regarding mixed injection operation. When it is determined that the approval button B15 has been depressed in S21, the inspection room side control section 9 and the adjustment room control section 19 make a judgment as to whether it is necessary to provide another prescription for the same patient or not (S23); when it is determined that there is another prescription (YES in S23), the procedure returns to S14, and details on the next prescription are displayed, repeating the mixed injection procedures thereafter. When it is determined that there is no following processing (NO in S23), it means the prescription for this patient has been completed, and the worker advances to the final inspection as illustrated in FIG. 3 (S15 (see FIG. 3)).

Further, the inspection room side control section 9 and the adjustment room control section 19 make a judgment, from the data accumulated in the medicine management server 1, as to whether there is a request for mixed injection inspection for another patient by a mixed injection worker, that is, whether other prescription data illustrated in S1 has been input by another worker (S26). Here, when it is determined that no other work has been input, the procedure returns to S1 (see FIG. 3), and the next input is waited for. When it is determined that there is some other work, the inspection room side control section 9 cuts off the connection with the control portion 19 of this work room 33, and connects to the control portion 19 of another work room designated in another work (S27). As a result, the procedure returns to S11. In this way, programming is effected such that the inspection room side control section 9 is only connected to one work room side control portion 19 at one time, and hence it is possible to prevent the inspector from making errors resulting from performing two inspections at the same time. By the above-mentioned procedures S11 through S26, the mixed injection work is executed. Then, as described above, each time one mixed injection work is completed, the final inspection as illustrated in S15 of FIG. 3 is conducted. The final inspection, which is performed to check the condition of the prepared solution, is conducted by the worker according to a manual from the viewpoint of form, color, etc. When the final inspection is complete, the prepared medicine is delivered to the pharmacy (S16).

BRIEF DESCRIPTION OF THE DRAWINGS

Figure 6:
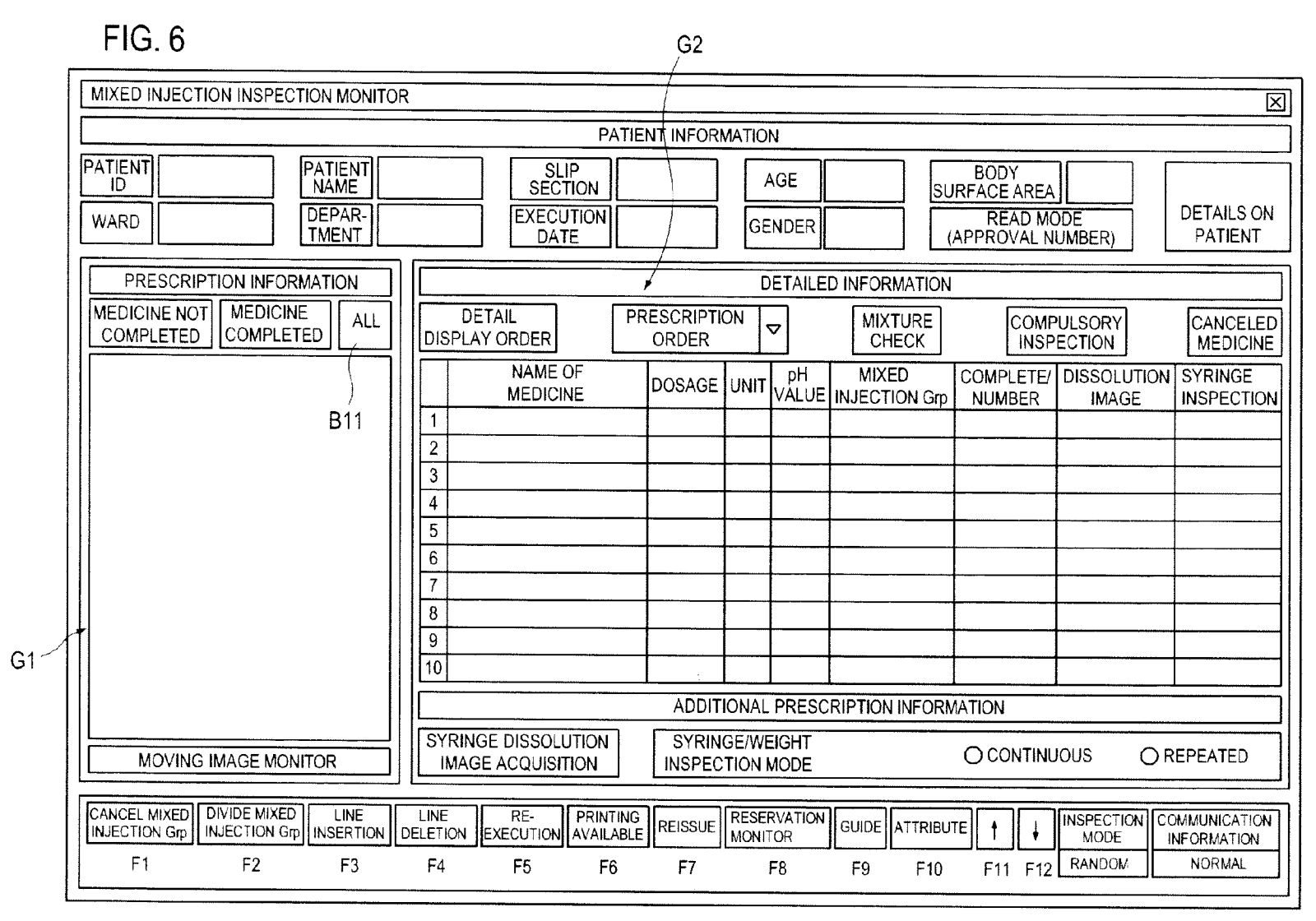

FIG. 6 A diagram illustrating an example of an initial screen when a mixed injection inspection monitor menu or a remote inspection monitor menu is selected in the mixed injection worker side display means or the inspector side mixed injection work monitor.

FIG. 7 A diagram illustrating how patient information is displayed on the mixed injection worker side display means or the inspector side mixed injection work monitor.

FIG. 8 A diagram illustrating a screen displaying a syringe constituting an inspection object.

Figure 9:
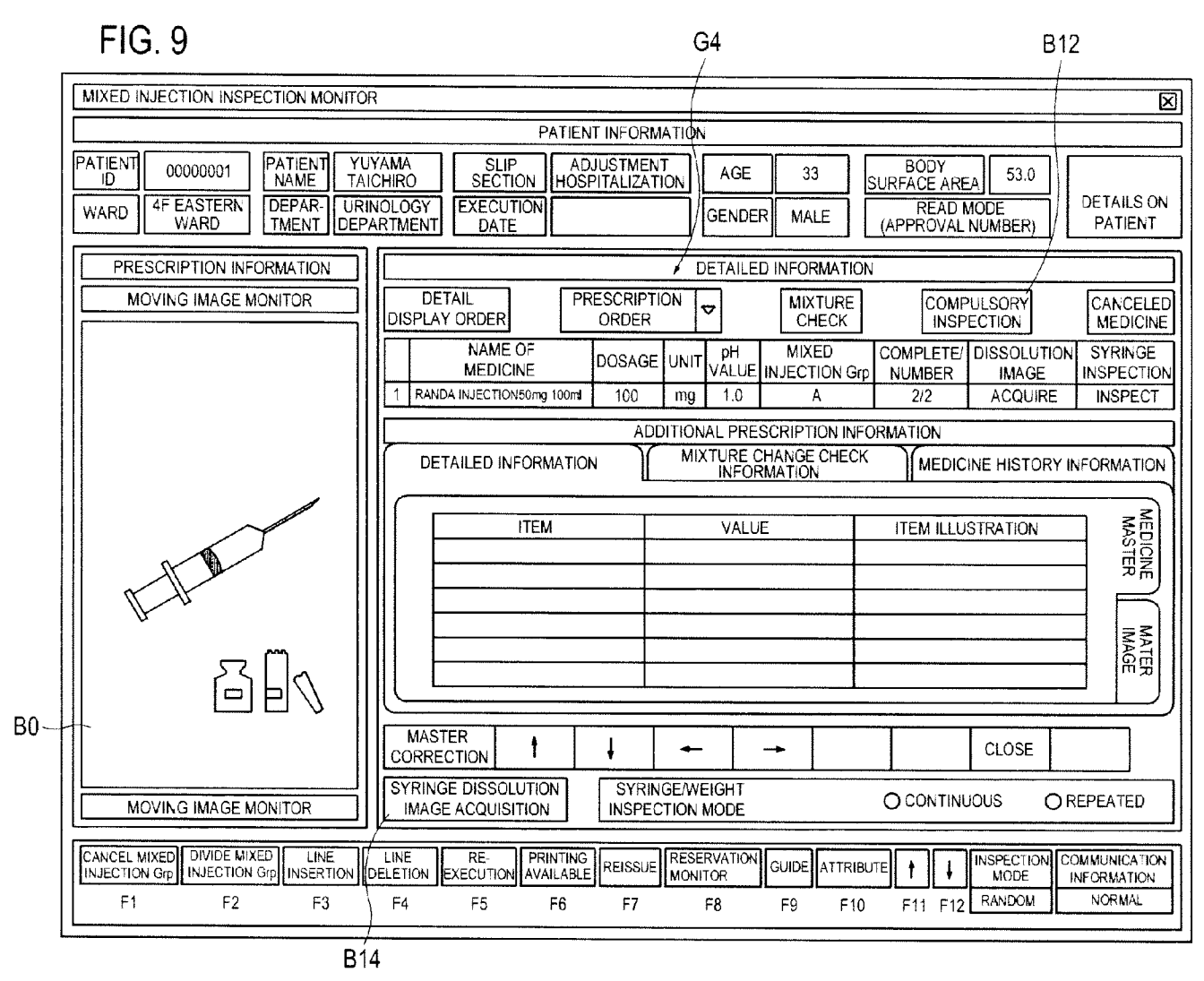

FIG. 9 A diagram illustrating a screen displaying detailed mixed injection information in the state of FIG. 8.

DESCRIPTION OF REFERENCE SYMBOLS

Figure 1:
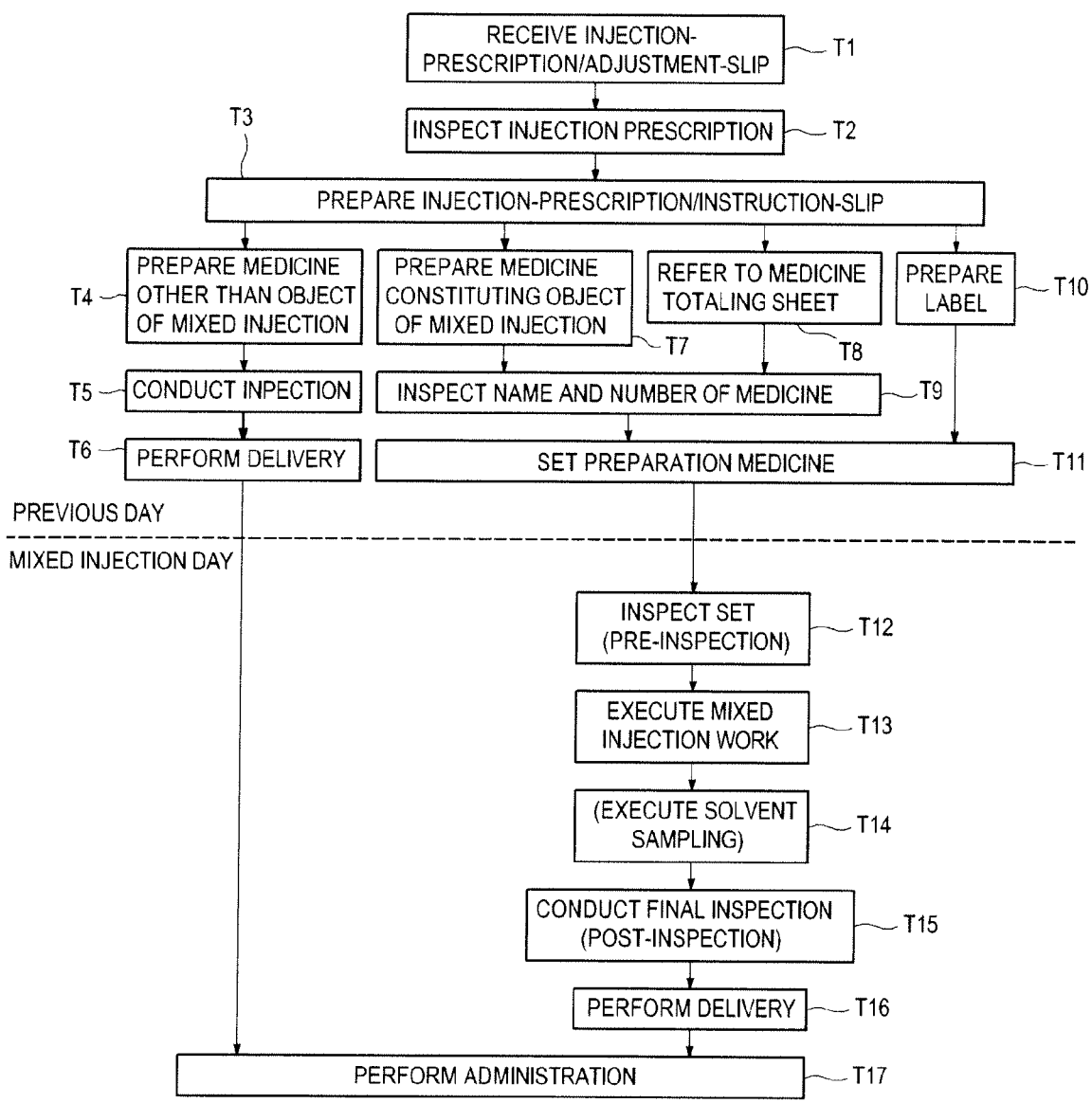
FIG. 1 A schematic flowchart to which the system of the present invention is applicable, illustrating the procedures of request for injection drug prescription to injection drug administration.
Figure 2:
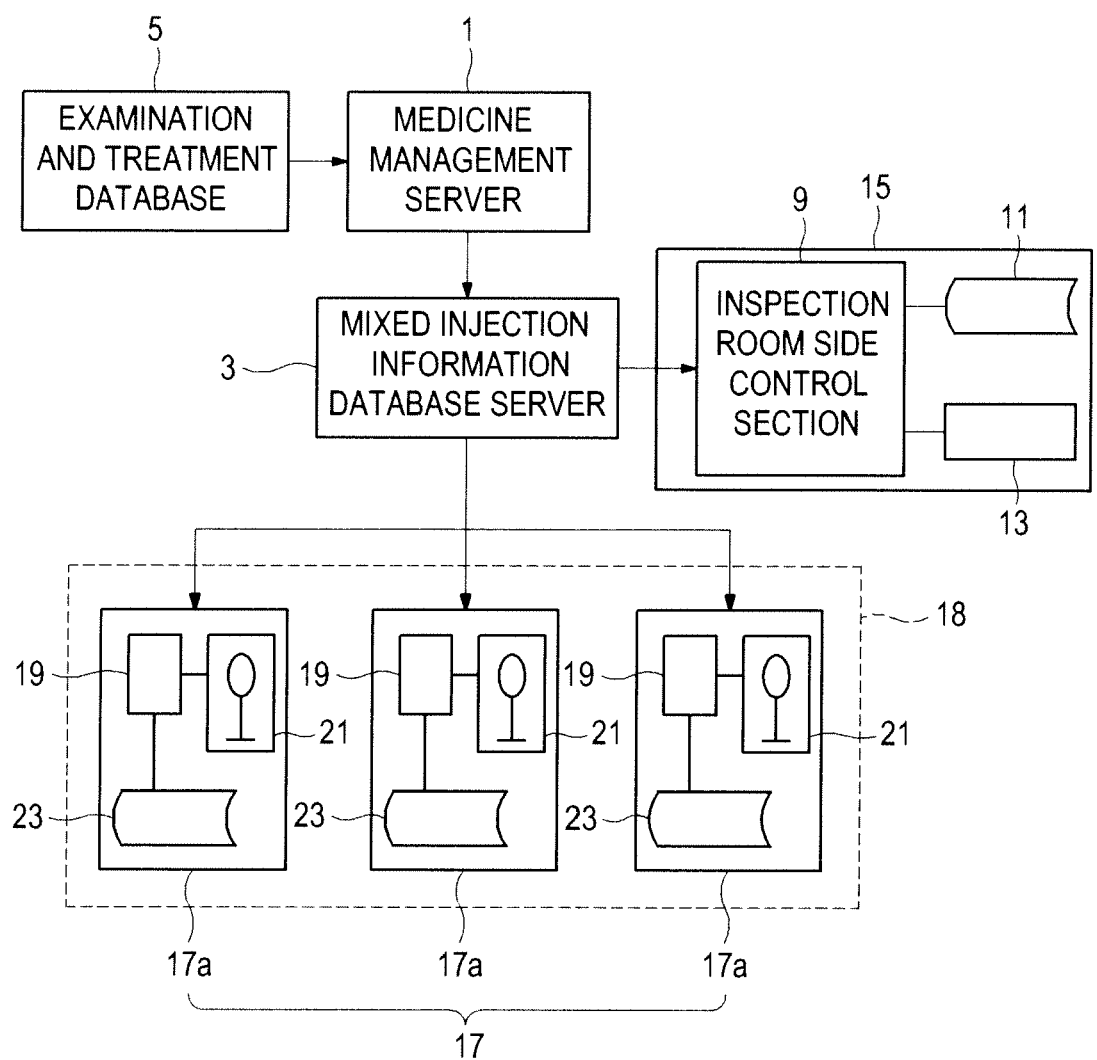
FIG. 2 A schematic diagram illustrating hardware for supporting the system of the present invention.
Figure 3:
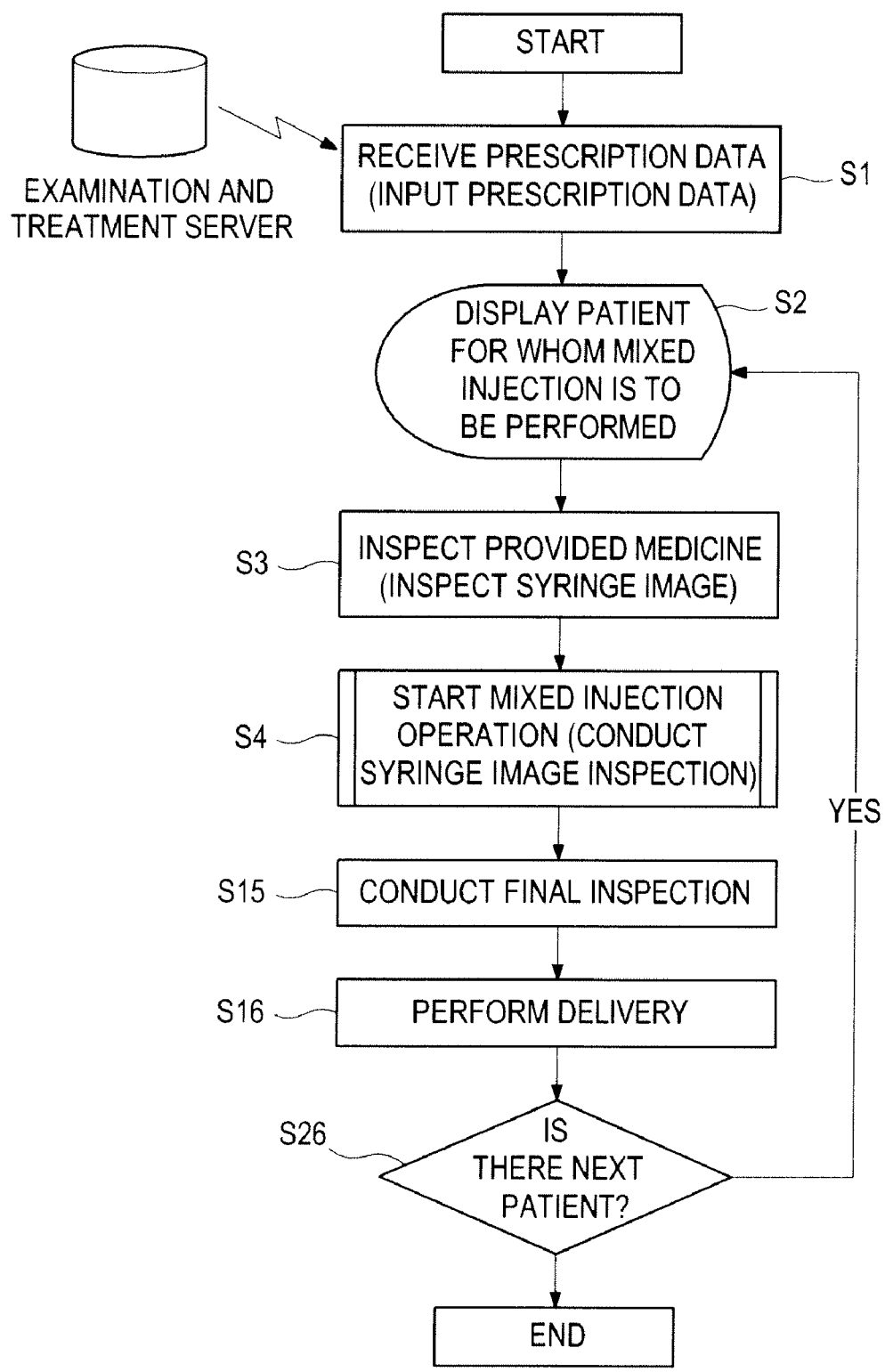
FIG. 3 A schematic flowchart illustrating mixed injection work.
Figure 4:
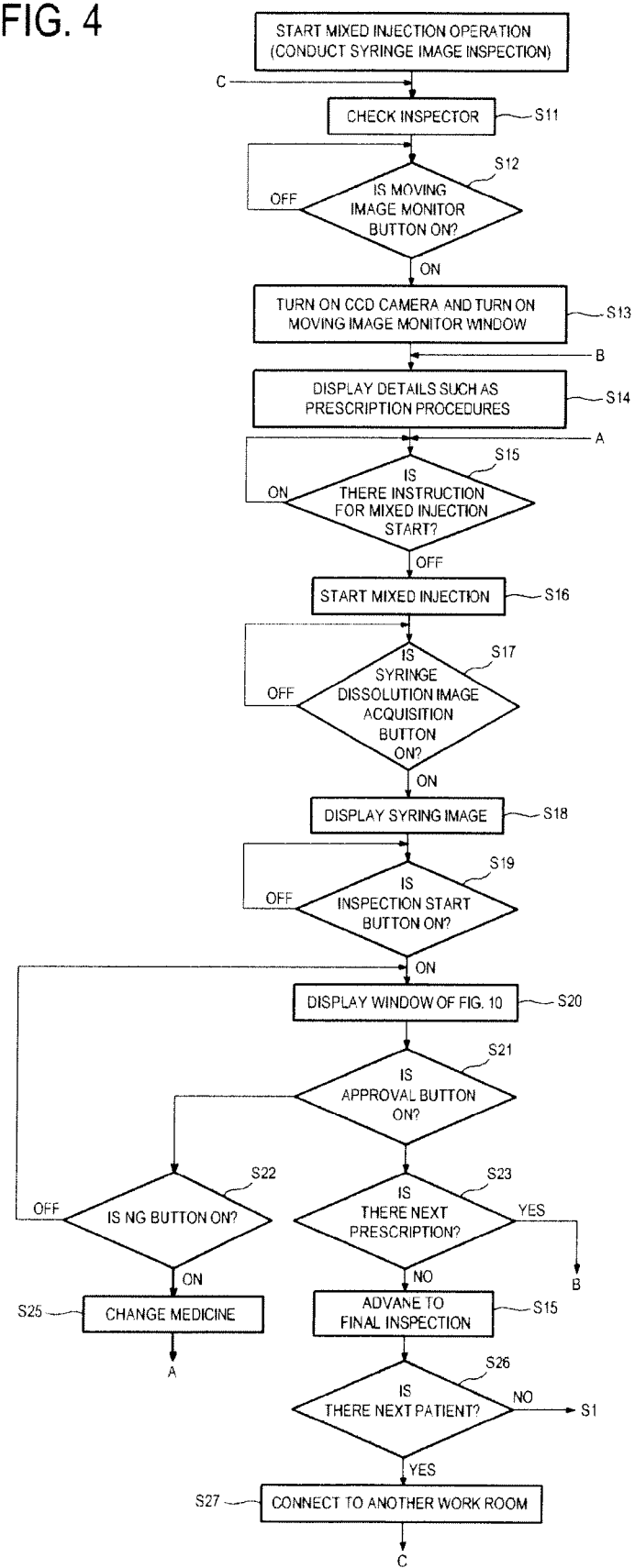
FIG. 4 A flowchart illustrating information processing procedures of a medicine management server supporting mixed injection work and a mixed injection worker side display means in relation to a control means.
Figure 5:
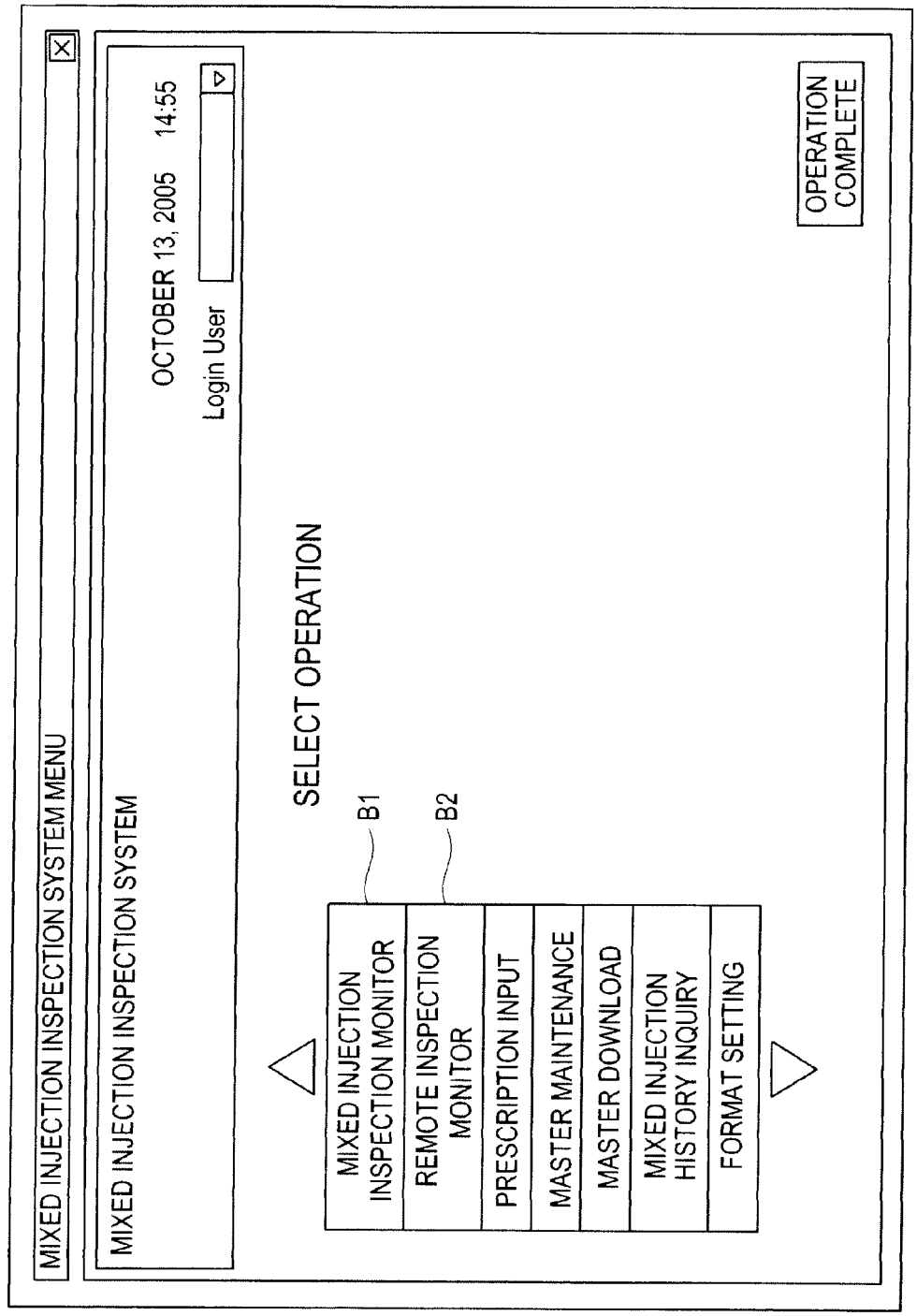
FIG. 5 A diagram illustrating an initial menu in a mixed injection worker side display means or an inspector side mixed injection work monitor.
Figure 10:
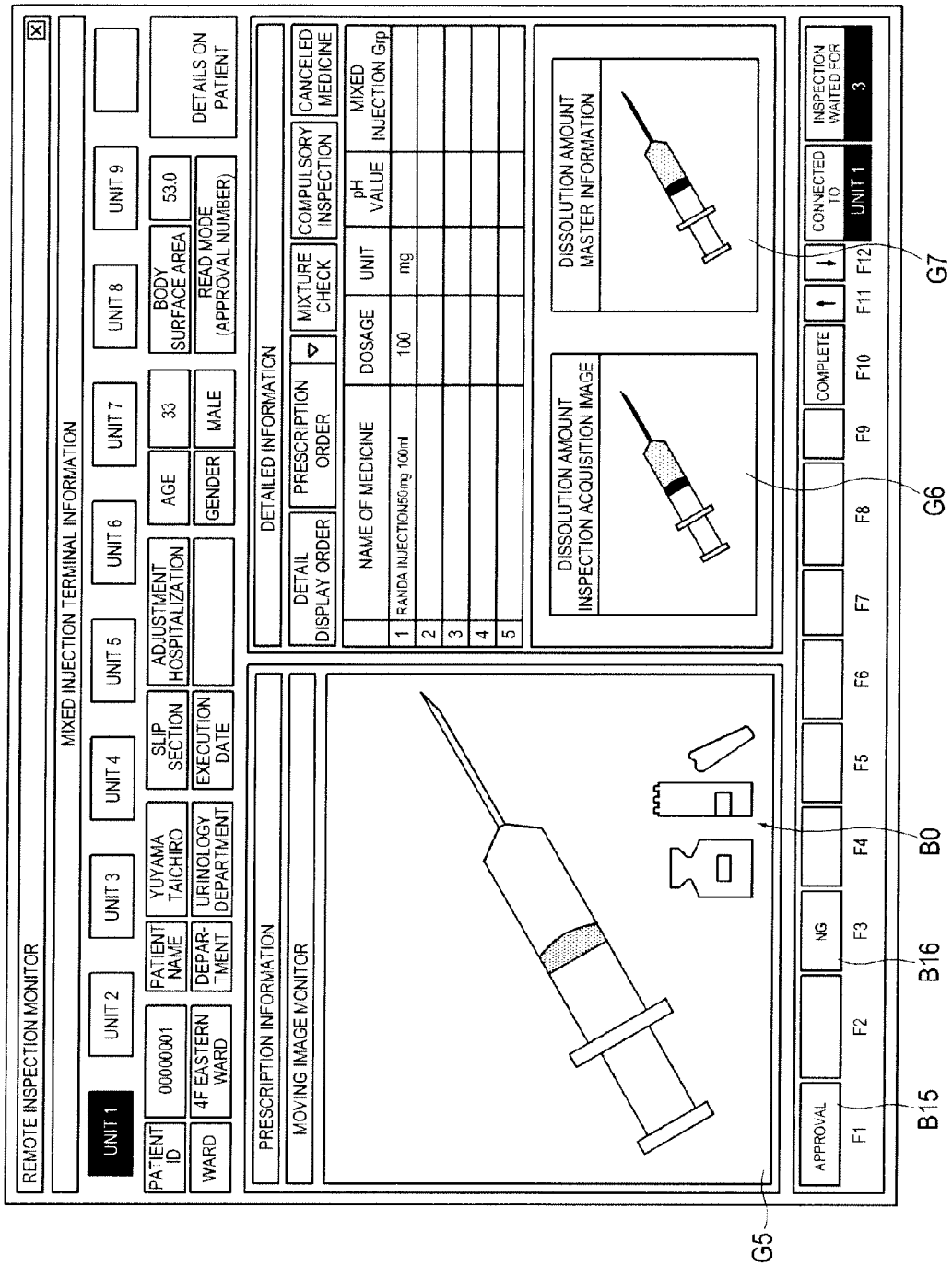
FIG. 10 A diagram illustrating the display screen of a remote inspection monitor.
Figure 11:
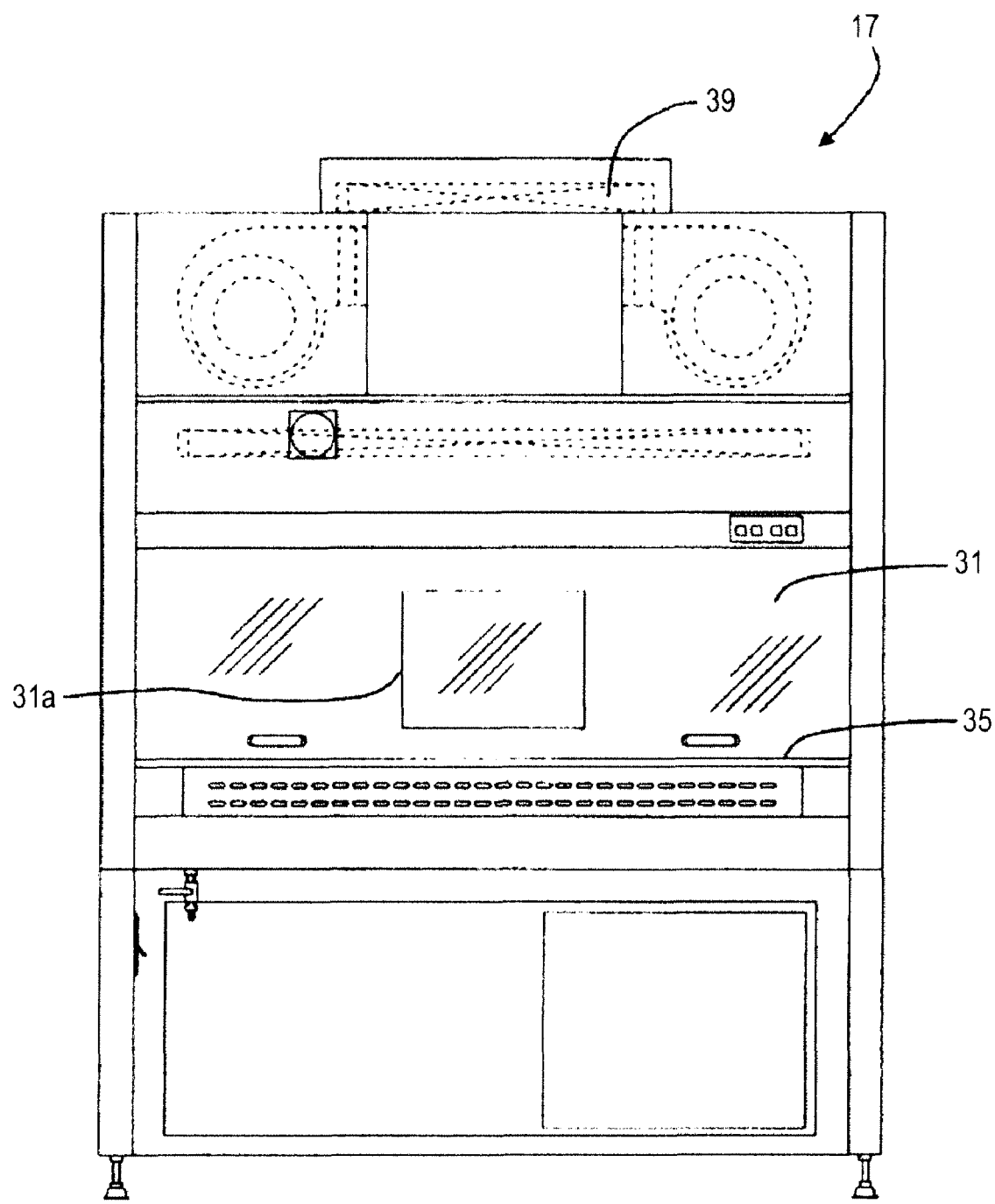
FIG. 11 A front view of an example of a safety cabinet for use in mixed injection work.
Figure 12:
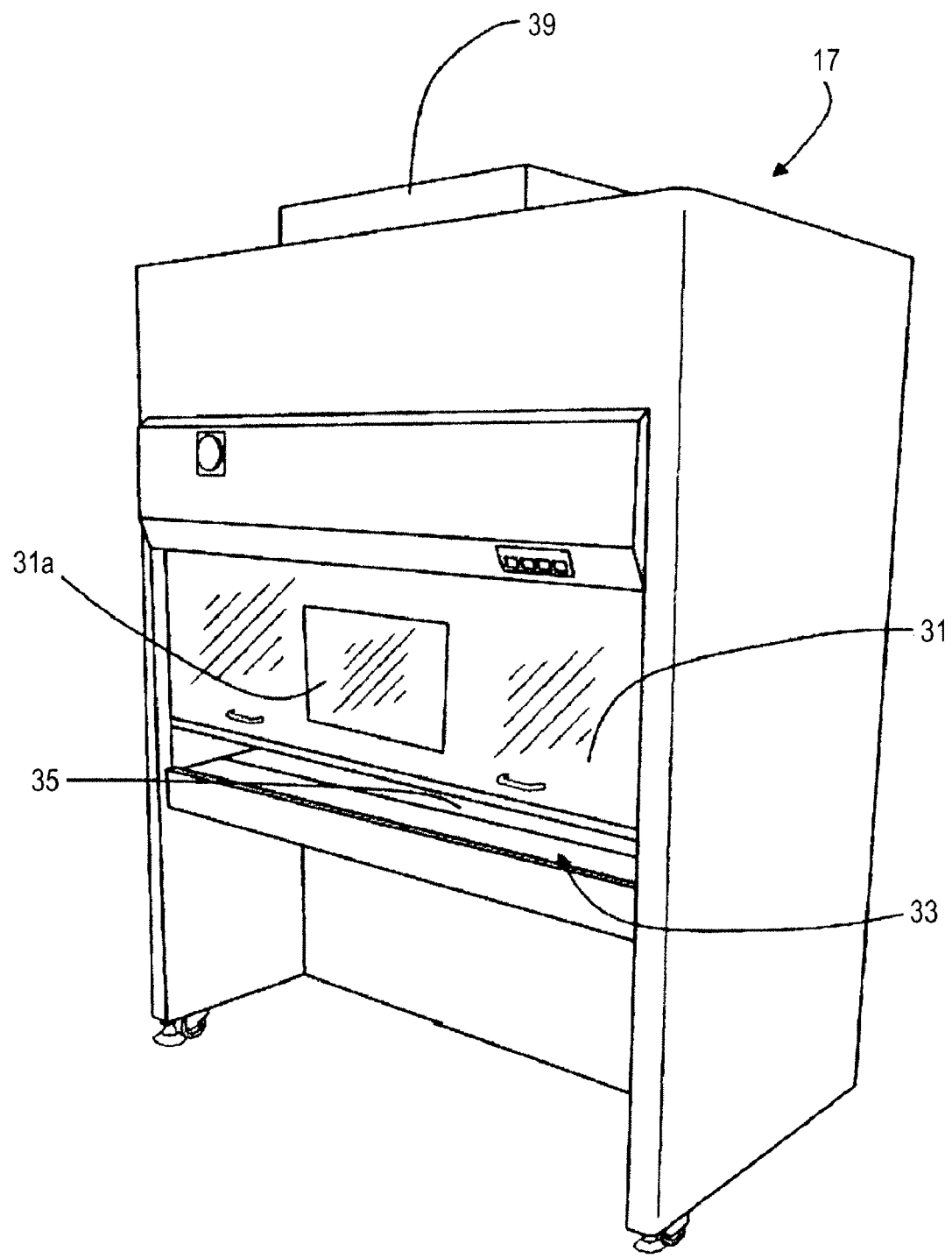
FIG. 12 A perspective view of the safety cabinet illustrated in FIG. 11.
Figure 13:
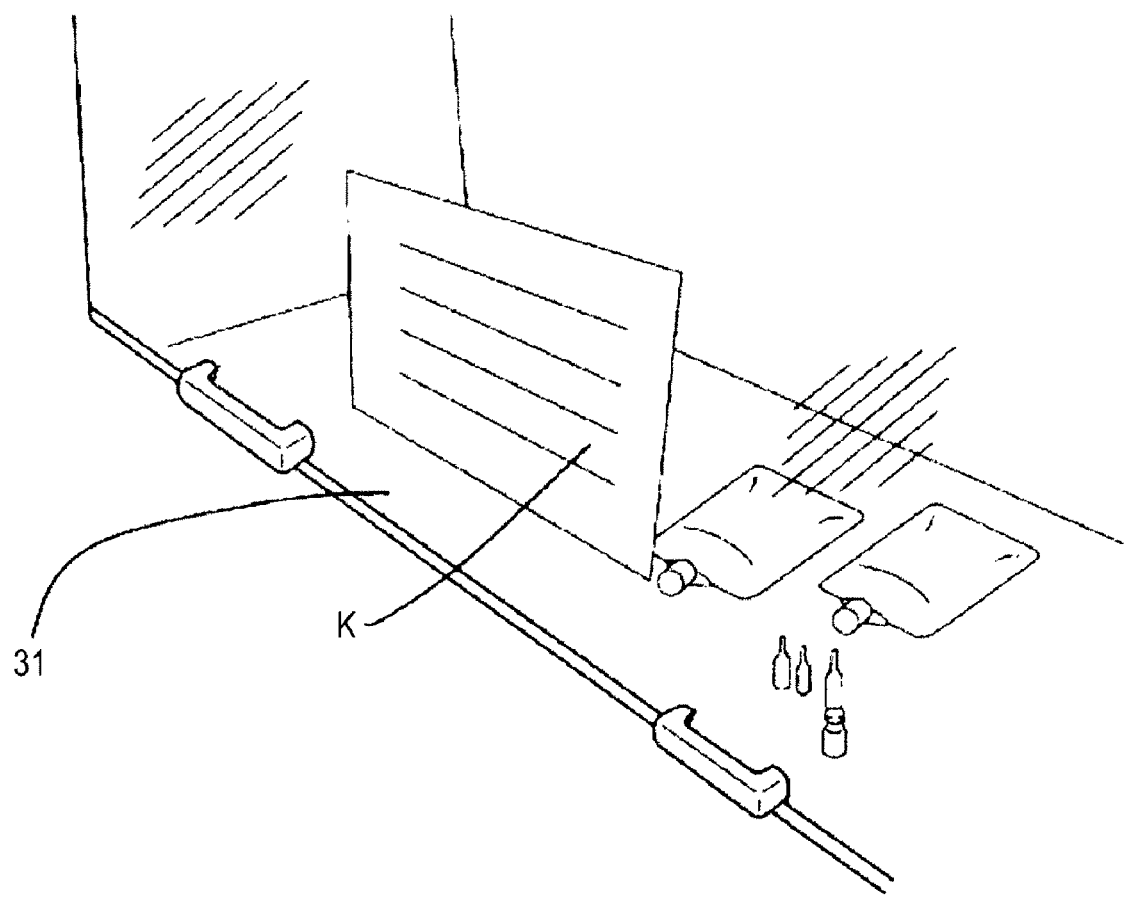
FIG. 13 A perspective view illustrating in detail the door portion of the safety cabinet.
Figure 14:
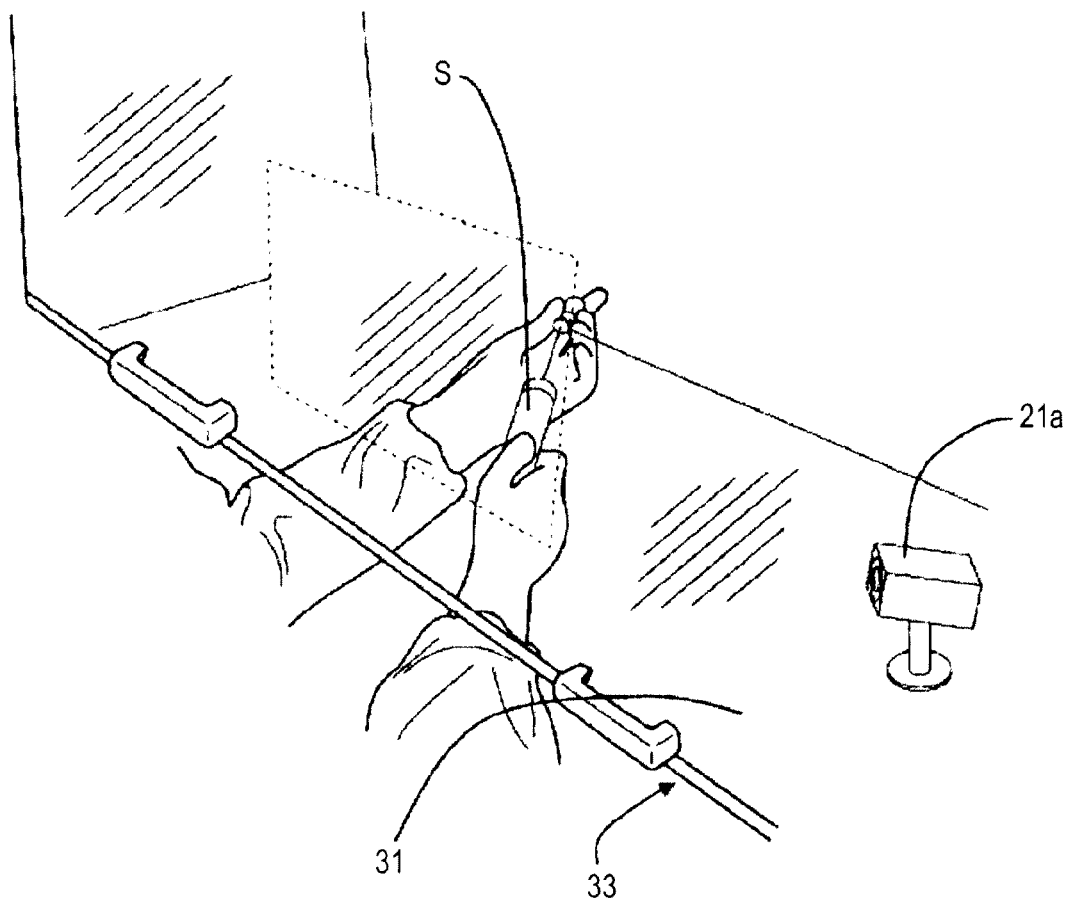
FIG. 14 A perspective view illustrating how work is conducted in the safety cabinet.
Figure 15:
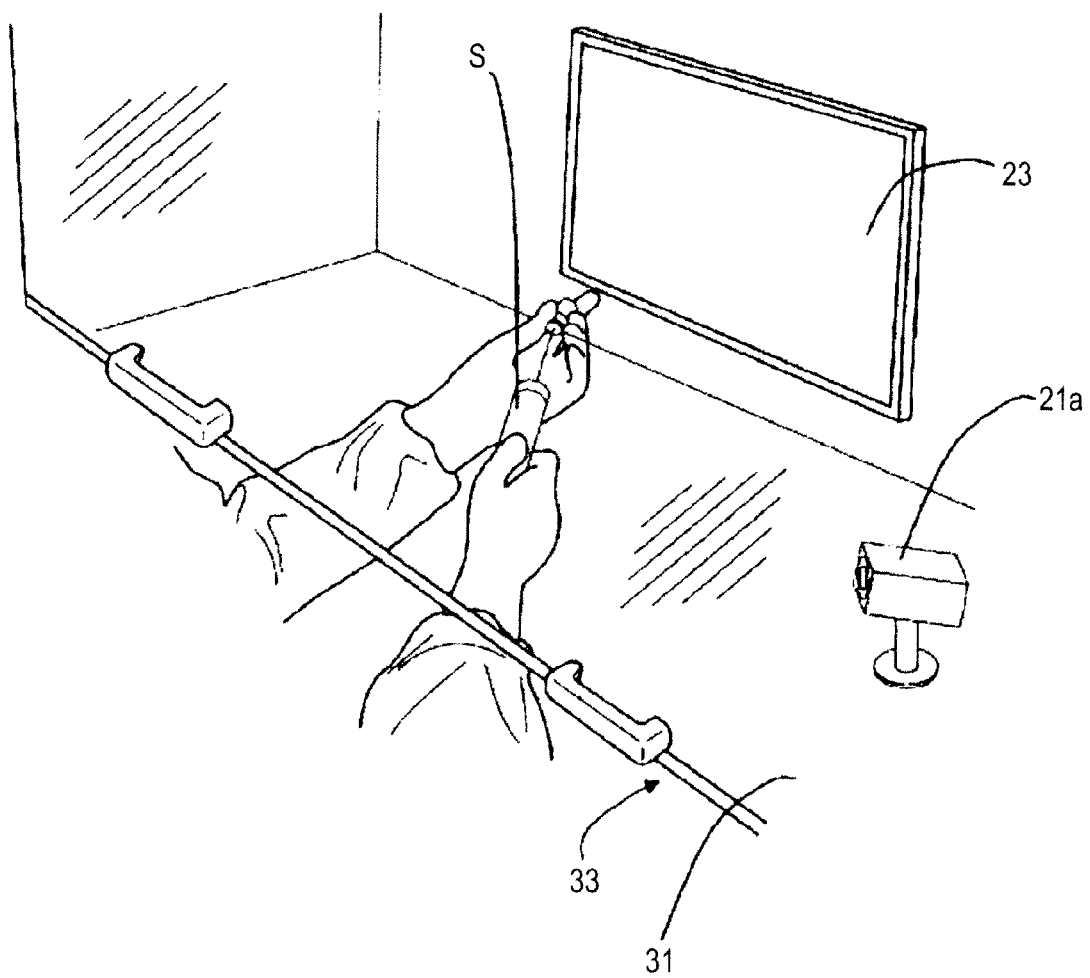
FIG. 15 A perspective view illustrating how work is conducted in another safety cabinet.
Figure 16:
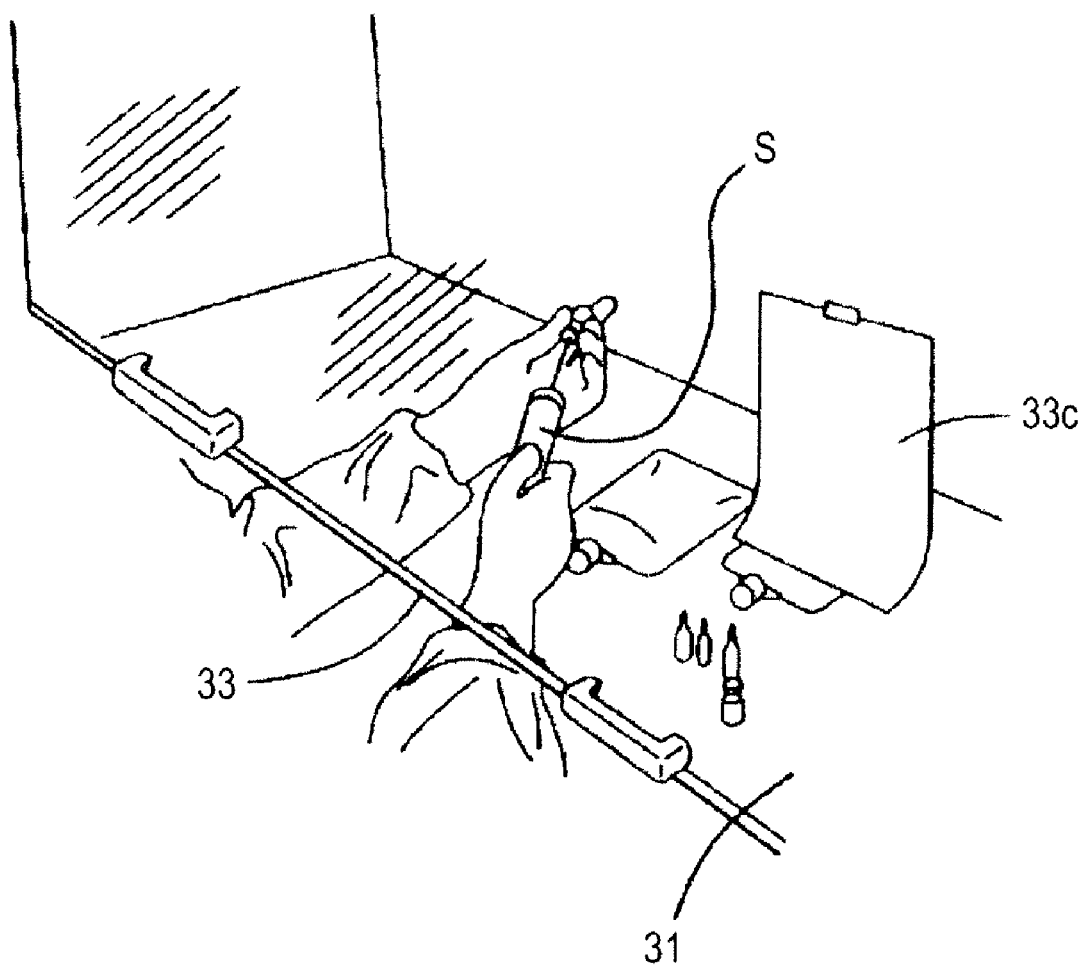
FIG. 16 A perspective view illustrating how work is conducted in still another safety cabinet.
Figure 17:
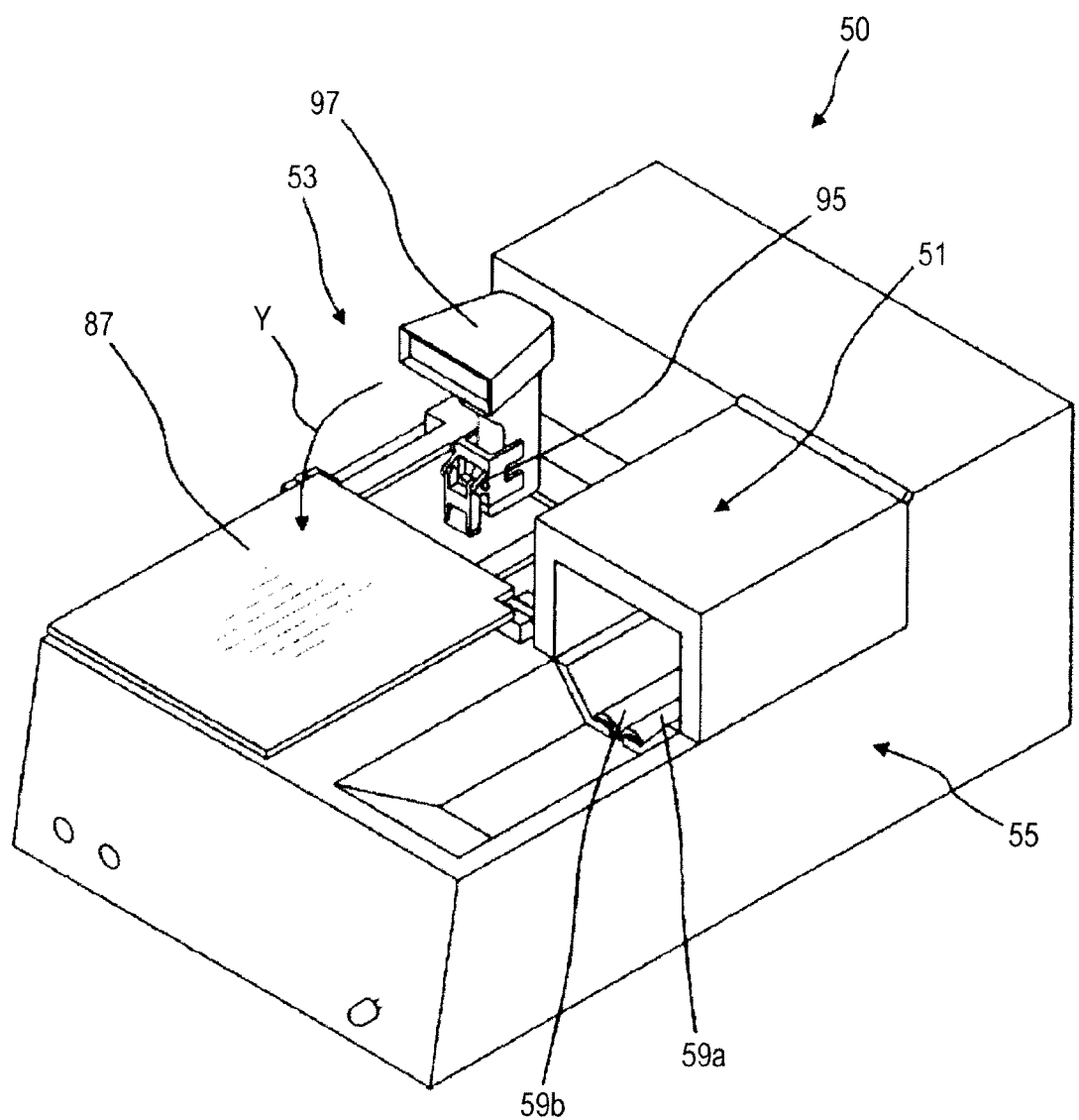
FIG. 17 A general perspective view of a pre-inspection apparatus.
Figure 18:
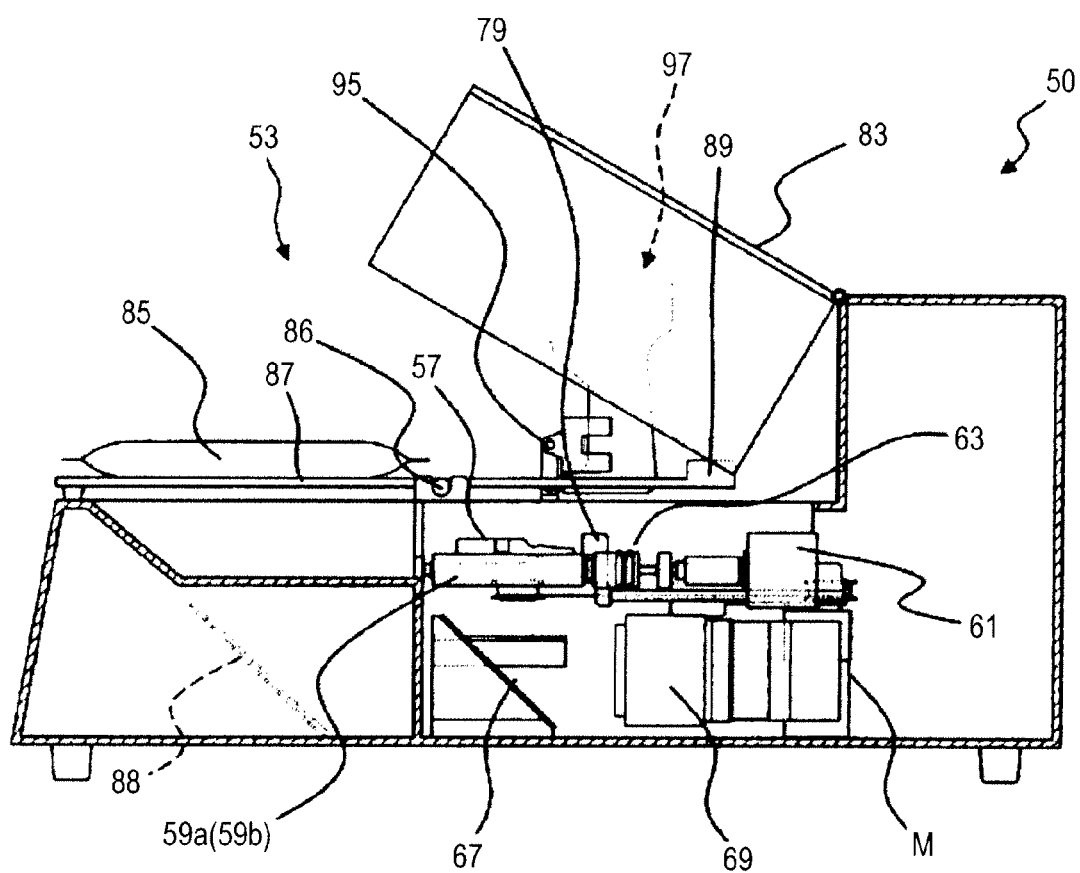
FIG. 18 A front view of the pre-inspection apparatus.
Figure 19:
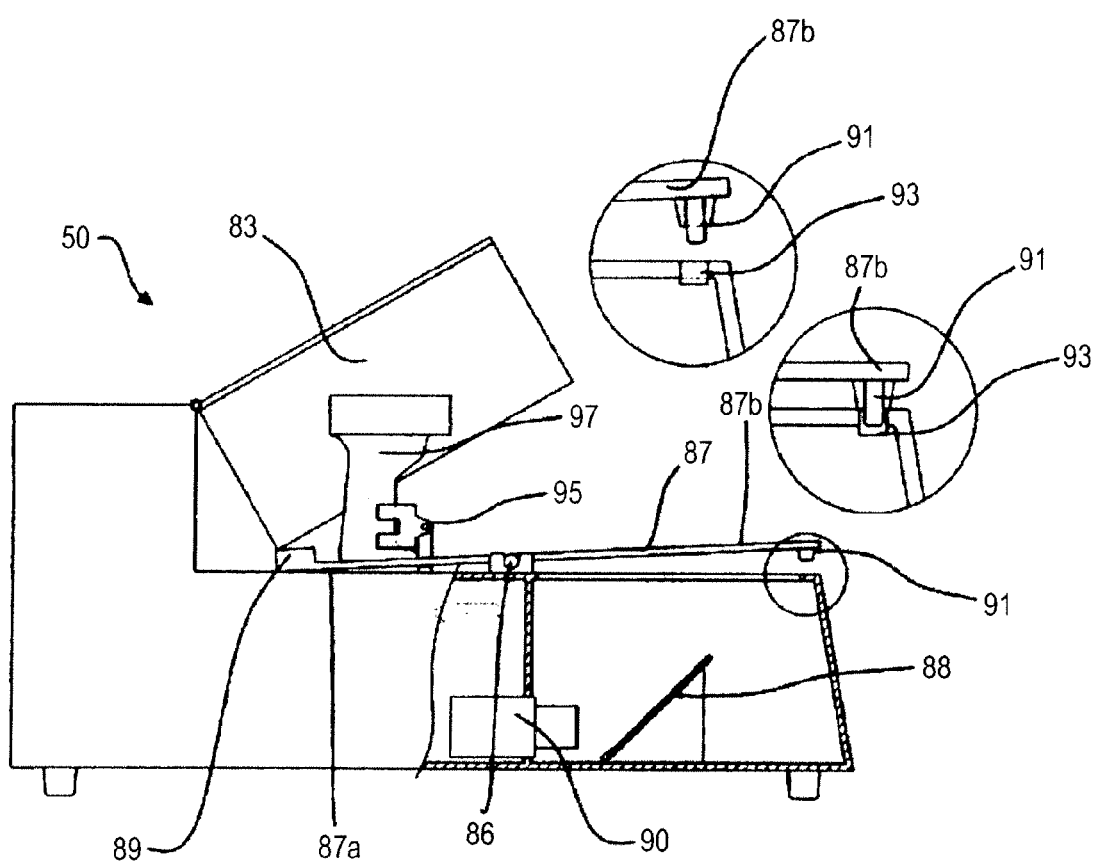
FIG. 19 A rear view of the pre-inspection apparatus.
Figure 20:
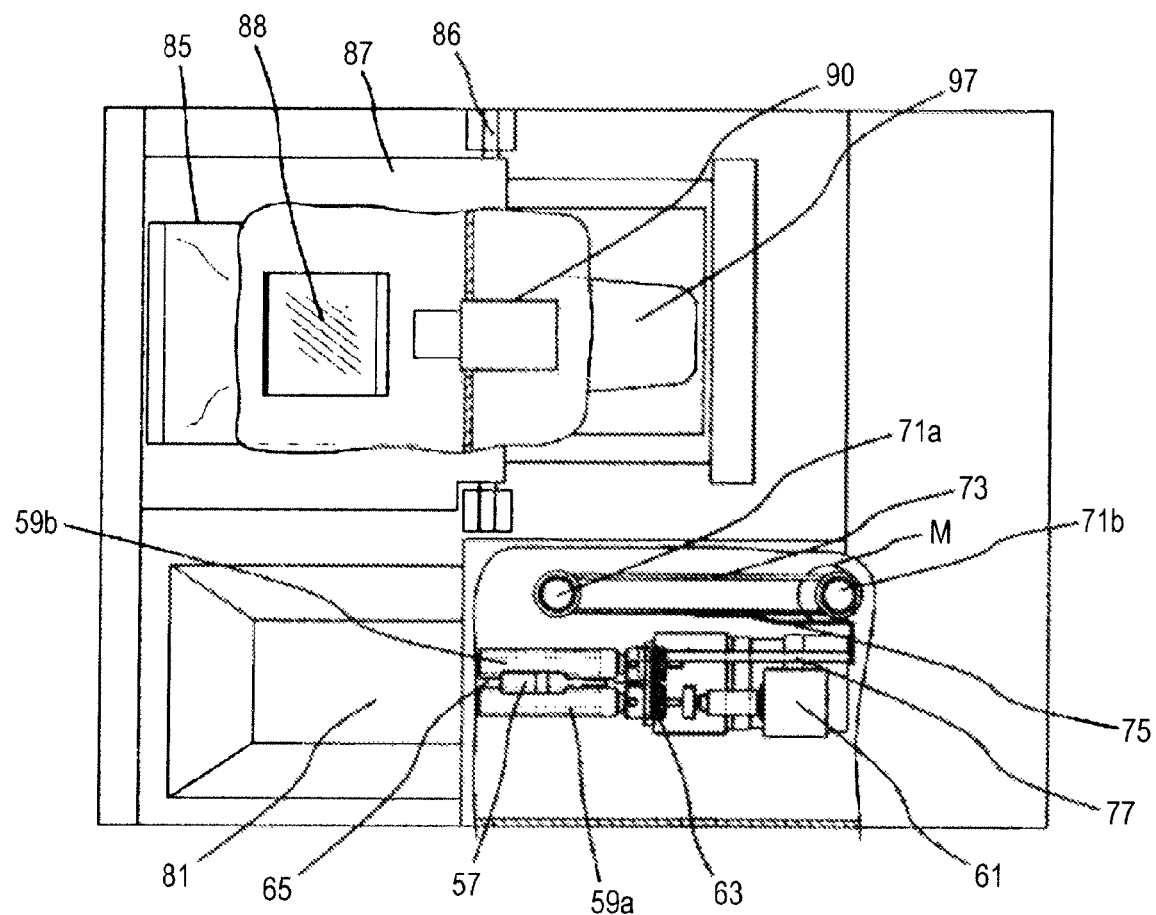
FIG. 20 A plan view of the pre-inspection apparatus.

1 . . . medicine management server, 3 . . . mixed injection information database, 9 . . . inspection room side control section, 11 . . . inspector side mixed injection work monitor, 13 . . . inspector side input device, 15 . . . inspection room, 17 . . . adjustment room, 18 . . . clean room, 19 . . . adjustment room control section, 21 . . . mixed injection work photographing device, 23 . . . mixed injection worker side display means, B1, B2 . . . button, S1, S2 . . . processing procedure (step) number, 50 . . . pre-inspection apparatus, 51 . . . medicine inspection portion, 53 . . . infusion bag inspection portion, 55 . . . lower drive portion, 57 . . . ampoule, 59a, 59b . . . rotary roller, 61 . . . speed reduction motor, 63 . . . belt, 65 . . . space, 67 . . . reflection mirror, 69 . . . line camera, 71a, 71b . . . pulley, 73 . . . belt, 75 . . . bracket, 79 . . . ampoule push-out member, 81 . . . box, 83 . . . cover, 85 . . . infusion solution bag, 86 . . . support bar, 87 . . . bag placing tray, 89 . . . weight, 91 . . . detection member, 93 . . . photo sensor, 95 . . . pin, 97 . . . barcode reader.

The invention claimed is:

1. An inspection system for remotely inspecting preparation of a drug at a mixing site, the inspection system comprising:
an imaging device provided at the mixing site, the imaging device configured to record an image associated with preparation of the drug;
a monitor provided at a location remote from the mixing site, the monitor configured to display the image recorded by the imaging device;
an input device associated with the monitor, the input device configured to input instructions for a worker working at the mixing site; and
a display located at the mixing site, the display configured to display the instructions input at the input device,
wherein the mixing site comprises a safety cabinet, and
wherein the imaging device is located within the safety cabinet.

2. The inspection system of claim 1, further comprising:
a server storing information about a medicine for use in preparation of the drug; and
an information monitor provided at the mixing site, the information monitor being connected to the server to display the information.

3. The inspection system of claim 2, wherein a single display serves as both the information monitor and the display.

4. The inspection system of claim 1, wherein the monitor displays a plurality of images from the imaging device.

5. The inspection system of claim 4, wherein the monitor enables an inspector to select for display an image from amongst the plurality of images.

6. The inspection system of claim 4, wherein the monitor displays the plurality of images responsive to a request input using an input device associated with the display at the mixing site.

7. The inspection system of claim 5, wherein the monitor enables the display to display selected images from amongst the plurality of images responsive to a request input using an input device associated with the display at the mixing site.

8. The inspection system of claim 1, wherein the monitor is further configured to display images sent from imaging devices located at a plurality of remote mixing sites.

9. The inspection system of claim 1, further comprising:
an image acquisition button provided at the mixing site,
wherein, responsive to the worker depressing the image acquisition button, the imaging device records an image of a syringe used in preparation of the drug.

10. The inspection system of claim 1, wherein the drug comprises a liquid medicine mixed with an infusion solution.

11. The inspection system of claim 10, wherein a first barcode is affixed to a surface of a container containing the liquid medicine and a second barcode is affixed to a surface of a container containing the infusion solution, the inspection system further comprising a programmed routine that determines whether the liquid medicine properly may be combined with the infusion solution based on the first and second barcodes.

12. The inspection system of claim 1, wherein the imaging device comprises a CCD.

13. An inspection system for remotely inspecting preparation of a drug at a mixing site, the inspection system comprising:
an imaging device provided at the mixing site, the imaging device configured to record an image associated with preparation of the drug;
a monitor provided at a location remote from the mixing site, the monitor configured to display the image recorded by the imaging device;
an input device associated with the monitor, the input device configured to input instructions for a worker working at the mixing site; and
a display located at the mixing site, the display configured to display the instructions input at the input device,
wherein the mixing site comprises a safety cabinet, and
wherein the display comprises a liquid crystal display disposed within the safety cabinet.

14. The inspection system of claim 1, wherein the monitor and the display both display at least some common data.

15. The inspection system of claim 1, wherein the imaging device is configured to obtain moving images or still images.

16. The inspection system of claim 1, wherein the input device comprises a microphone.

17. The inspection system of claim 2, wherein the server stores at least one image associated with preparation of the drug.

18. The inspection system of claim 8, wherein, at a given time, the monitor displays images received from only a selected one of the plurality of mixing sites.

19. An inspection system for remotely inspecting preparation of a drug at a mixing site, the inspection system comprising:
an imaging device provided at the mixing site, the imaging device configured to record an image associated with preparation of the drug;
a monitor provided at a location remote from the mixing site, the monitor configured to display the image recorded by the imaging device;

an input device associated with the monitor, the input device configured to input instructions for a worker working at the mixing site; and
a display located at the mixing site, the display configured to display the instructions input at the input device,
wherein the mixing site comprises a clean bench, and
wherein the imaging device is located within the clean bench.

* * * * *